United States Patent
Plaza et al.

(10) Patent No.: US 11,690,629 B2
(45) Date of Patent: *Jul. 4, 2023

(54) SYSTEMS AND METHODS FOR DELIVERY OF STENTS AND STENT-LIKE DEVICES

(71) Applicant: MICROVENTION, INC., Aliso Viejo, CA (US)

(72) Inventors: Claudio Plaza, Rancho Santa Margarita, CA (US); James M. Thompson, Lake Forest, CA (US); Hung P. Tran, Midway City, CA (US)

(73) Assignee: MICROVENTION, INC., Aliso Viejo, CA (US)

( * ) Notice: Subject to any disclaimer, the term of this patent is extended or adjusted under 35 U.S.C. 154(b) by 147 days.

This patent is subject to a terminal disclaimer.

(21) Appl. No.: 17/176,744

(22) Filed: Feb. 16, 2021

(65) Prior Publication Data
US 2021/0275188 A1     Sep. 9, 2021

Related U.S. Application Data

(63) Continuation of application No. 15/453,581, filed on Mar. 8, 2017, now Pat. No. 10,952,739.
(Continued)

(51) Int. Cl.
*A61B 17/12* (2006.01)
*A61F 2/966* (2013.01)
(Continued)

(52) U.S. Cl.
CPC .. *A61B 17/12118* (2013.01); *A61B 17/12109* (2013.01); *A61B 17/12172* (2013.01);
(Continued)

(58) Field of Classification Search
CPC ...... A61F 2/86; A61F 2/90; A61F 2/91; A61F 2/95; A61F 2/962; A61F 2/966;
(Continued)

(56) References Cited

U.S. PATENT DOCUMENTS 5,951,569 A    9/1999 Tuckey et al.
6,080,177 A    6/2000 Igaki et al.
(Continued)

OTHER PUBLICATIONS

WO, PCT/US17/21577 ISR and Written Opinion, dated May 25, 2017.

*Primary Examiner* — Todd J Scherbel
(74) *Attorney, Agent, or Firm* — ONE LLP

(57) ABSTRACT

Systems for treating an aneurysm in a cerebral vessel and methods of use are described. In one embodiment, the system includes an elongate tubular member having a lumen, an expandable stent, and a delivery device. The expandable stent has a constrained state that is configured for delivery through the lumen of the elongate tubular member, and an expanded state configured for placement within the cerebral vessel adjacent the aneurysm. The delivery device includes an elongate member and a self-expandable portion. The proximal end of the self-expandable portion is coupled to the elongate member at or near the distal end of the elongate member. The self-expandable portion of the delivery device includes a tubular mesh structure having a constrained state and an expanded state. The stent is engaged (e.g., mechanical, frictional, or intermeshing) with the self-expandable portion of the delivery device.

19 Claims, 16 Drawing Sheets

Related U.S. Application Data

(60) Provisional application No. 62/307,123, filed on Mar. 11, 2016.

(51) Int. Cl.
*A61F 2/90* (2013.01)
*A61F 2/82* (2013.01)
*A61B 17/00* (2006.01)

(52) U.S. Cl.
CPC ...... *A61F 2/90* (2013.01); *A61B 2017/00836* (2013.01); *A61B 2017/1205* (2013.01); *A61F 2002/823* (2013.01); *A61F 2210/0009* (2013.01); *A61F 2310/00029* (2013.01)

(58) Field of Classification Search
CPC ...... A61F 2002/9505; A61F 2002/9511; A61F 2002/9528; A61F 2002/9534; A61F 2002/9665
See application file for complete search history.

(56) References Cited

U.S. PATENT DOCUMENTS

| | | | |
|---|---|---|---|
| 8,043,353 | B2 | 10/2011 | Kaufmann et al. |
| 9,078,658 | B2 | 7/2015 | Hewitt et al. |
| 9,597,087 | B2 | 3/2017 | Marchand et al. |
| 10,952,739 | B2 * | 3/2021 | Plaza ............... A61B 17/12172 |
| 2005/0125052 | A1 | 6/2005 | Iwata et al. |
| 2005/0278011 | A1 | 12/2005 | Peckham |
| 2006/0184226 | A1 | 8/2006 | Austin |
| 2006/0190070 | A1 | 8/2006 | Dieck et al. |
| 2006/0200234 | A1 | 9/2006 | Hines |
| 2007/0055351 | A1 | 3/2007 | Eidenschink et al. |
| 2008/0082165 | A1 | 4/2008 | Wilson et al. |
| 2009/0216309 | A1 | 8/2009 | Granada et al. |
| 2011/0082490 | A1 | 4/2011 | Connelly et al. |
| 2011/0276121 | A1 | 11/2011 | Levine |
| 2012/0203325 | A1 | 8/2012 | Weisman et al. |
| 2012/0271407 | A1 | 10/2012 | Jones et al. |
| 2012/0316632 | A1 | 12/2012 | Gao |
| 2013/0018452 | A1 | 1/2013 | Weitzner et al. |
| 2013/0297003 | A1 | 11/2013 | Pinchuk |
| 2014/0088689 | A1 | 3/2014 | Bales, Jr. et al. |
| 2014/0180387 | A1 | 6/2014 | Khenansho et al. |
| 2014/0303543 | A1 | 10/2014 | Meade et al. |
| 2014/0358178 | A1 | 12/2014 | Hewitt et al. |
| 2017/0079817 | A1 | 3/2017 | Sepetka et al. |
| 2017/0258473 | A1 | 9/2017 | Plaza et al. |

* cited by examiner

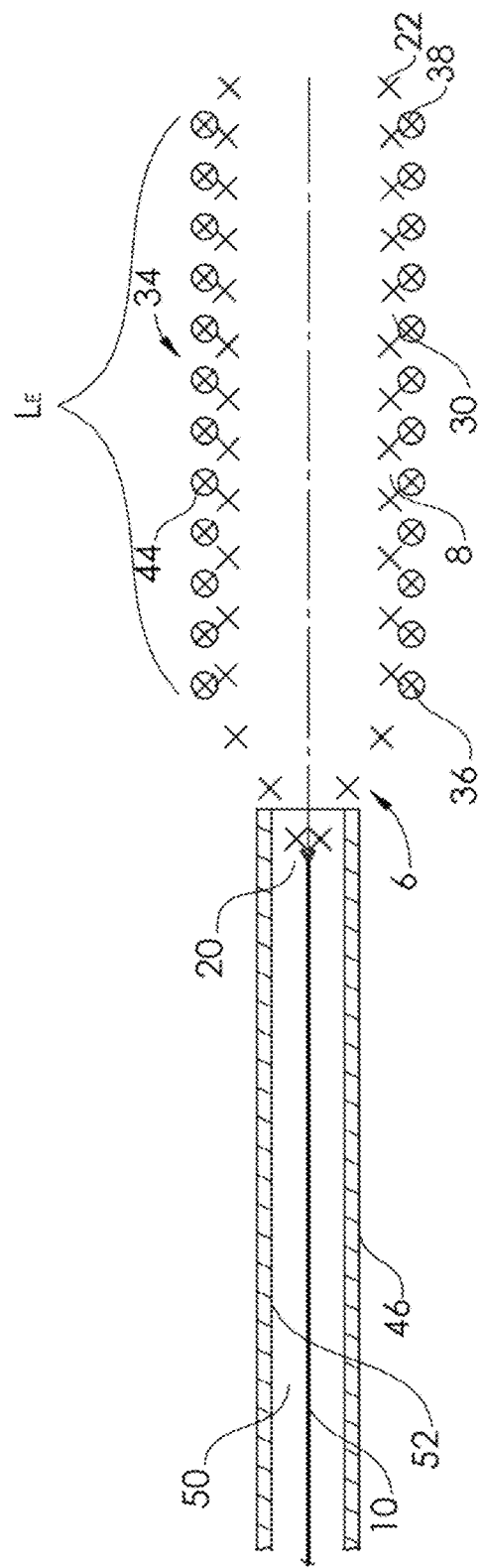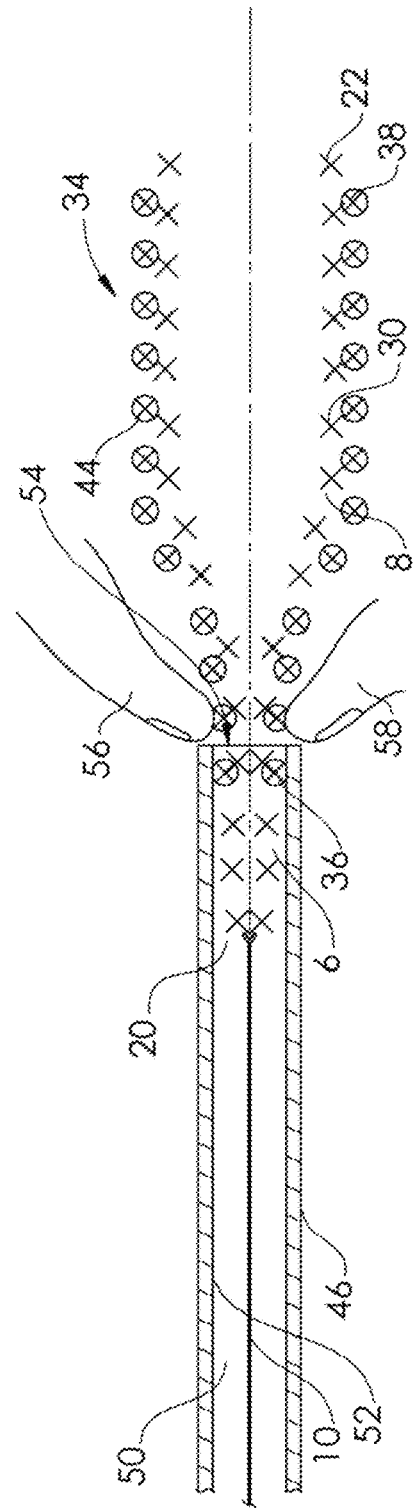
FIG. 7
FIG. 8

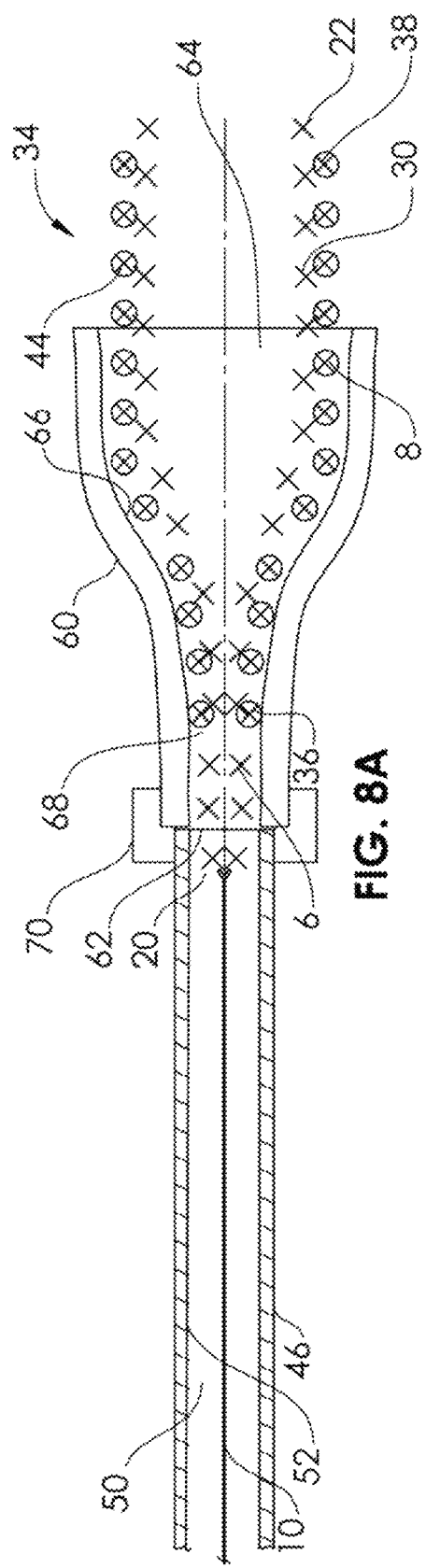
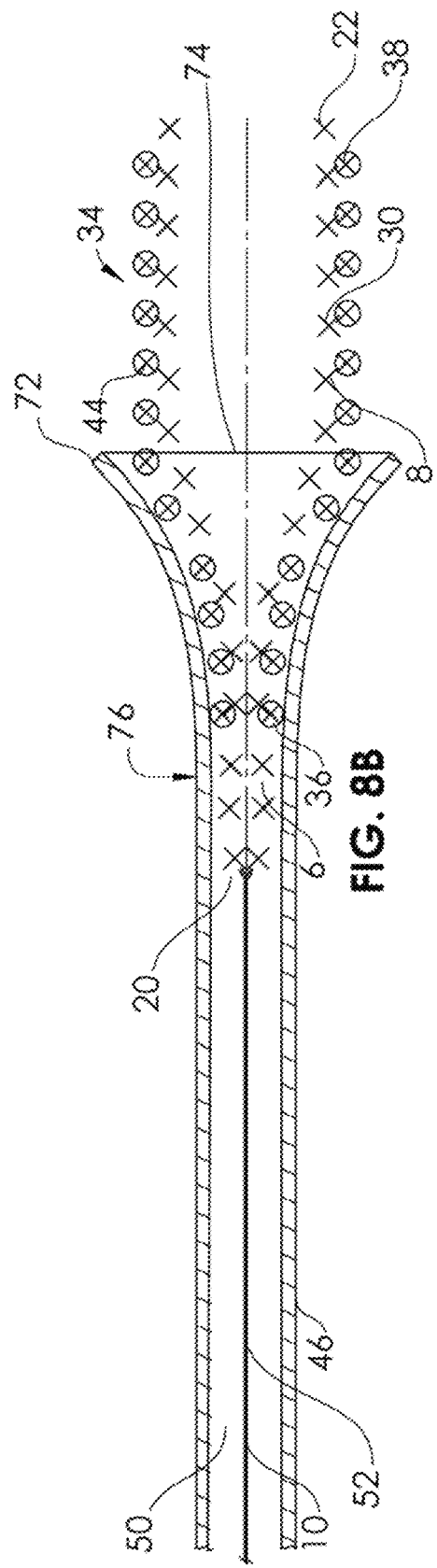

SYSTEMS AND METHODS FOR DELIVERY OF STENTS AND STENT-LIKE DEVICES

RELATED APPLICATIONS

This application is a continuation of U.S. application Ser. No. 15/453,581, filed Mar. 8, 2017, which claims priority under 35 U.S.C. § 119(e) to U.S. Provisional Application Ser. No. 62/307,123, filed Mar. 11, 2016, entitled "Systems and Methods for Delivery of Stents and Stent-like Devices," all of which are herein expressly incorporated by reference in their entirety for all purposes.

FIELD OF THE INVENTION

Embodiments of devices and methods herein are directed to blocking a flow of fluid through a tubular vessel or into a small interior chamber of a saccular cavity or vascular defect within a mammalian body. More specifically, embodiments herein are directed to devices and methods for treatment of a vascular defect of a patient including some embodiments directed specifically to the treatment of cerebral aneurysms of patients.

BACKGROUND

The mammalian circulatory system is comprised of a heart, which acts as a pump, and a system of blood vessels which transport the blood to various points in the body. Due to the force exerted by the flowing blood on the blood vessel, the blood vessels may develop a variety of vascular defects. One common vascular defect known as an aneurysm results from the abnormal widening of the blood vessel. Typically, vascular aneurysms are formed as a result of the weakening of the wall of a blood vessel and subsequent ballooning and expansion of the vessel wall. If, for example, an aneurysm is present within an artery of the brain, and the aneurysm should burst with resulting cranial hemorrhaging, death could occur.

Surgical techniques for the treatment of cerebral aneurysms typically involve a craniotomy requiring creation of an opening in the skull of the patient through which the surgeon can insert instruments to operate directly on the patient's brain. For some surgical approaches, the brain must be retracted to expose the parent blood vessel from which the aneurysm arises. Once access to the aneurysm is gained, the surgeon places a clip across the neck of the aneurysm thereby preventing arterial blood from entering the aneurysm. Upon correct placement of the clip the aneurysm will be obliterated in a matter of minutes. Surgical techniques may be effective treatment for many aneurysms. Unfortunately, surgical techniques for treating these types of conditions include major invasive surgical procedures which often require extended periods of time under anesthesia involving high risk to the patient. Such procedures thus require that the patient be in generally good physical condition in order to be a candidate for such procedures.

Various alternative and less invasive procedures have been used to treat cerebral aneurysms without resorting to major surgery. Some such procedures involve the delivery of embolic or filling materials into an aneurysm. The delivery of such vaso-occlusion devices or materials may be used to promote hemostasis or fill an aneurysm cavity entirely. Vaso-occlusion devices may be placed within the vasculature of the human body, typically via a catheter, either to block the flow of blood through a vessel with an aneurysm through the formation of an embolus or to form such an embolus within an aneurysm stemming from the vessel. A variety of implantable, coil-type vaso-occlusion devices are known. The coils of such devices may themselves be formed into a secondary coil shape, or any of a variety of more complex secondary shapes. Vaso-occlusive coils are commonly used to treat cerebral aneurysms but suffer from several limitations including poor packing density, compaction due to hydrodynamic pressure from blood flow, poor stability in wide-necked aneurysms, and complexity and difficulty in the deployment thereof as most aneurysm treatments with this approach require the deployment of multiple coils. Recently, expandable mesh devices have been used to fill the volume of an aneurysm and to disrupt normal blood flow in the aneurysm.

Another approach to treating aneurysms without the need for invasive surgery involves the placement of sleeves or stents into the vessel and across the region where the aneurysm occurs. Such devices maintain blood flow through the vessel while reducing blood pressure applied to the interior of the aneurysm. Certain types of stents are expanded to the proper size by inflating a balloon catheter, referred to as balloon expandable stents, while other stents are designed to elastically expand in a self-expanding manner. Certain subsets of these devices are sometimes referred to as flow diversion devices. Some stents are covered typically with a sleeve of polymeric material called a graft to form a stent-graft. Stents and stent-grafts are generally delivered to a preselected position adjacent a vascular defect through a delivery catheter. In the treatment of cerebral aneurysms, covered stents or stent-grafts have seen very limited use due to the likelihood of inadvertent occlusion of small perforator vessels that may be near the vascular defect being treated.

In addition, current uncovered stents are generally not sufficient as a stand-alone treatment. In order for stents to fit through the microcatheters used in small cerebral blood vessels, their density is usually reduced such that when expanded there is only a small amount of stent structure bridging the aneurysm neck. Thus, they do not block enough flow to cause clotting of the blood in the aneurysm and are thus generally used in combination with vaso-occlusive devices, such as the coils discussed above, to achieve aneurysm occlusion.

A number of aneurysm neck bridging devices with defect spanning portions or regions have been attempted; however, none of these devices have had a significant measure of clinical success or usage. A major limitation in their adoption and clinical usefulness is the inability to position the defect spanning portion to assure coverage of the neck. Existing stent delivery systems that are neurovascular compatible (i.e., deliverable through a microcatheter and highly flexible) do not have the necessary rotational positioning capability. Another limitation of many aneurysm bridging devices described in the prior art is poor flexibility. Cerebral blood vessels are tortuous and a high degree of flexibility is required for effective delivery to most aneurysm locations in the brain.

SUMMARY

An embodiment of the invention includes a system for treating an aneurysm in a cerebral vessel. The system includes an elongate tubular member having a proximal end, a distal end, and a lumen therebetween having an inner diameter d. The system also includes an expandable stent having a proximal end, a distal end, and a lumen therebetween. The expandable stent has a constrained state with an outer diameter $od_1$ that is configured for delivery through the lumen of the elongate tubular member, and an expanded state having an inside diameter $id_2$ and an outer diameter $od_2$; $od_2$ is greater than $od_1$. The expanded state of the stent is configured for placement within the cerebral vessel adjacent the aneurysm. The system also includes a delivery device that includes an elongate member having proximal and distal ends, and a self-expandable portion having proximal and distal ends. The proximal end of the self-expandable portion may be coupled to the elongate member at or near the distal end of the elongate member. The self-expandable portion includes a tubular mesh structure having a constrained state with an outer diameter $OD_1$ that is configured for delivery through the lumen of the elongate tubular member, and an expanded state having an outer diameter $OD_2$. The stent is engaged with the self-expandable portion of the delivery device.

In alternative embodiments of the inventions, the stent may have different dimensions. In one embodiment, the inside diameter $id_2$ of the expanded state of the stent decreases between the proximal and distal ends of the stent. Alternatively, the inside diameter $id_2$ of the expanded state of the stent increases between the proximal and distal ends of the stent. Alternatively, the inside diameter $id_2$ of the expanded state of the stent is substantially the same between the proximal and distal ends of the stent. Alternatively, the inside diameter $id_2$ of the expanded state of the stent is between about 2 mm and about 5 mm. Alternatively, the inside diameter $id_2$ of the expanded state of the stent increases between about 0.5 mm and about 2.0 mm between the proximal and distal ends of the stent.

In alternative embodiments of the inventions, the stent may be made from a tubular mesh. Alternatively, the stent may be made from a slotted tube having a plurality of struts. The stent may be completely self-expanding or partially self-expanding. In an alternative embodiment, for the tubular mesh embodiment of the stent, a braid angle of the stent may be different than a braid angle of the self-expandable portion. Alternatively, a braid angle of the stent is substantially similar to a braid angle of the self-expandable portion.

In alternative embodiments of the inventions, the self-expandable portion of the delivery device may have different dimensions. The outer diameter $OD_2$ of the expanded state of the self-expandable portion of the delivery device may decrease between the distal and proximal ends. Alternatively, the expanded state of the self-expandable portion has a tubular portion having the outer diameter $OD_2$ over a length of at least 2 mm. Alternatively, the expanded state of the self-expandable portion has a tubular portion having the outer diameter $OD_2$ over a length of about 2 mm to about 15 mm. Alternatively, the expanded state of the self-expandable portion has a tubular portion having the outer diameter $OD_2$ over a length of about 3 mm to about 10 mm.

In alternative embodiments, at least part of the self-expandable portion of the delivery device is disposed within the lumen of the stent. In one embodiment, the at least part of the self-expandable portion mechanically engages at least a portion of the stent. In an alternative embodiment, the at least part of the self-expandable portion frictionally engages at least a portion of the stent. In an alternative embodiment, the at least part of the self-expandable portion mechanically engages at least a portion of the stent through intermeshing. In an alternative embodiment, the at least part of the self-expandable portion engages the stent substantially from the proximal end to the distal end of the stent. In an alternative embodiment, the at least part of the self-expandable portion mechanically engages the stent substantially from the proximal end to the distal end of the stent. In an alternative embodiment, the at least part of the self-expandable portion frictionally engages the stent substantially from the proximal end to the distal end of the stent.

In other embodiments of the invention, the tubular mesh of the self-expandable portion of the delivery device includes a plurality of filaments. In alternative embodiments, the plurality of filaments comprises a cobalt-chromium alloy. In alternative embodiments, at least a portion of the plurality of filaments comprises a cobalt-chromium alloy. In alternative embodiments, the plurality of filaments each have a diameter of between about 0.0010 inches and 0.0020 inches. In alternative embodiments, the plurality of filaments each has a diameter of between about 0.0013 inches and 0.0017 inches. In alternative embodiments, the plurality of filaments each have a diameter of about 0.0015 inches. In alternative embodiments, the plurality of filaments are braided. In alternative embodiments, the braided filaments have a braid angle of between about 75° and about 80°.

In another embodiment, a system for completely or partially excluding an aneurysm from circulation of blood is described. The system includes a microcatheter having a lumen, a fully or partially self-expandable stent, and a delivery device. The fully or partially self-expandable stent has a first end and a second end, and is configured to be deliverable through the lumen of the microcatheter. The stent also has a self-expanded inner diameter. The delivery device is configured to be deliverable together with the stent through the lumen of the microcatheter. The delivery device includes an elongate support member having a proximal end, a distal end, and a self-expandable portion having a proximal end and a distal end. The proximal end of the self-expandable portion is coupled at or near the distal end of the elongate support member. The self-expandable portion of the delivery device includes a tubular mesh structure having a compressed state and an expanded state. A distal portion of the self-expandable portion extends proximally from the distal end of the self-expandable portion and has a length having an expanded outer diameter. The proximal end of the self-expandable portion is substantially non-expanded where it is coupled to the elongate support member. The expanded outer diameter of the distal portion of the self-expandable portion is equal to or greater than the self-expanded inner diameter of the stent.

In another embodiment, the invention includes a delivery device configured to deliver a medical implant through the lumen of a catheter. The delivery device includes an elongate support member having a proximal end and a distal end, and a self-expandable portion having a proximal end and a distal end. The proximal end of the self-expandable portion is coupled at or near the distal end of the elongate support member. The self-expandable portion includes a tubular mesh structure having a compressed state and an expanded state. A distal portion of the self-expandable portion extends proximally from the distal end of the self-expandable portion and has a length having an expanded outer diameter. The proximal end of the self-expandable portion is substantially non-expanded where it is coupled to the elongate support member. The expanded outer diameter of the distal portion of the self-expandable portion is equal to or greater than a maximum inner diameter of the medical implant.

The invention also includes various methods of treatment. In alternative embodiments, methods for treating an aneurysm in a cerebral vessel using the stents and delivery devices described in the various embodiments above are also described. The method includes the step of providing a microcatheter having a proximal end, a distal end, a lumen extending therebetween, a distal opening communicating with the lumen, and an inner diameter d. A system comprising an expandable stent and a delivery device, as described in the various embodiments above, is provided. The distal end of the microcatheter is advanced to a position distal to a neck of the aneurysm. The system is advanced within the lumen of the microcatheter, wherein both the expandable stent and self-expandable portion are each in the constrained state within the lumen of the microcatheter. At least part of the stent and at least part of the self-expandable portion of the delivery device are then released through the distal opening of the microcatheter, wherein the distal end of the stent is located in the cerebral vessel distal of the aneurysm neck.

In alternative embodiments, the step of releasing at least part of the stent and at least part of the self-expandable portion of the delivery device can be carried out in different ways. The releasing step may occur by advancing the distal end of the stent and the distal end of the self-expandable portion of the delivery device through the distal opening of the microcatheter. Alternatively, the releasing step may occur by withdrawing the microcatheter proximally while the elongate member of the delivery device is held substantially in place, wherein the stent and self-expandable portion of the delivery device expand to their expanded states.

In alternative embodiments, a method for treating an aneurysm in a cerebral vessel using the stents described in the various embodiments above may include the additional step of assessing the placement of the stent relative to the aneurysm neck (e.g., using a contrast (dye) injection).

In alternative embodiments, where the physician is dissatisfied with the placement of the device, the method can further include the step of recapturing the at least part of the stent and at least part of the self-expandable portion within the lumen of the microcatheter. The step of recapturing the at least part of the stent and at least part of the self-expandable portion of the delivery device may include the step of advancing the microcatheter distally while maintaining traction on the elongate member of the delivery device to recapture the stent and self-expandable portion within the lumen of the microcatheter. Additionally, the distal end of the microcatheter can then be repositioned to a position distal of a neck of the aneurysm. The stent and at least part of the self-expandable portion of the delivery device can then be released through the distal opening of the microcatheter, wherein the stent in its expanded state is positioned in the cerebral vessel such that the distal end of the stent is located distal of the aneurysm neck and the proximal end of the stent is located proximal of the aneurysm neck.

In alternative embodiments, the step of recapturing the at least part of the stent and at least part of the self-expandable portion includes the step of advancing the microcatheter distally while maintaining traction on the elongate member of the delivery device to recapture the stent and self-expandable portion within the lumen of the microcatheter.

In alternative embodiments, the method includes the step of advancing the microcatheter distally while applying traction to the proximal end of the elongate member of the delivery device, thereby disengaging the stent and the self-expandable portion, and withdrawing the self-expandable portion of the delivery device into the lumen of the microcatheter.

In alternative embodiments, methods for treating an aneurysm in a cerebral vessel using the stents described in the various embodiments above are also described. The method includes the step of providing a microcatheter having a proximal end, a distal end, a lumen extending therebetween, a distal opening communicating with the lumen, and an inner diameter d. A system comprising an expandable stent and a delivery device, as described in the various embodiments above, is provided. The distal end of the microcatheter is advanced to a position distal to a neck of the aneurysm. The system is advanced within the lumen of the microcatheter, wherein both the expandable stent and self-expandable portion are each in the constrained state within the lumen. At least part of the stent and at least part of the self-expandable portion of the delivery device are then released through the distal opening of the microcatheter, wherein the distal end of the stent is located in the cerebral vessel distal of the aneurysm neck. At least part of the stent and at least part of the self-expandable portion is then recaptured within the lumen of the microcatheter. The distal end of the microcatheter is repositioned to a position distal of a neck of the aneurysm. The at least part of the stent and at least part of the self-expandable portion of the delivery device are then released through the distal opening of the microcatheter, wherein the stent and self-expandable portion of the delivery device expand to their expanded states, wherein the stent in its expanded state is positioned in the cerebral vessel such that the distal end of the stent is located distal of the aneurysm neck and the proximal end of the stent is located proximal of the aneurysm neck.

BRIEF DESCRIPTION OF THE DRAWINGS

FIG. 7 is a sectional view of the delivery device and the mesh therapeutic device fully coupled together in longitudinal alignment.

FIG. 8 is a sectional view of the delivery device and the mesh therapeutic device being inserted within the introducer sheath.

FIG. 8A is a sectional view showing an alternative insertion technique to that of FIG. 8.

FIG. 8B is a sectional view showing an alternative insertion technique to that of FIG. 8.

DETAILED DESCRIPTION

Discussed herein are devices and methods for the treatment of vascular defects that are suitable for minimally invasive deployment within a patient's vasculature, and particularly, within the cerebral vasculature of a patient. For such embodiments to be safely and effectively delivered to a desired treatment site and effectively deployed, some device embodiments may be configured for collapse to a low profile constrained state with a transverse dimension suitable for delivery through an inner lumen of a microcatheter and deployment from a distal end thereof. Unless otherwise stated, one or more of the features, dimensions, or materials of the various embodiments may be used in other similar embodiments discussed herein.

Figure 1:
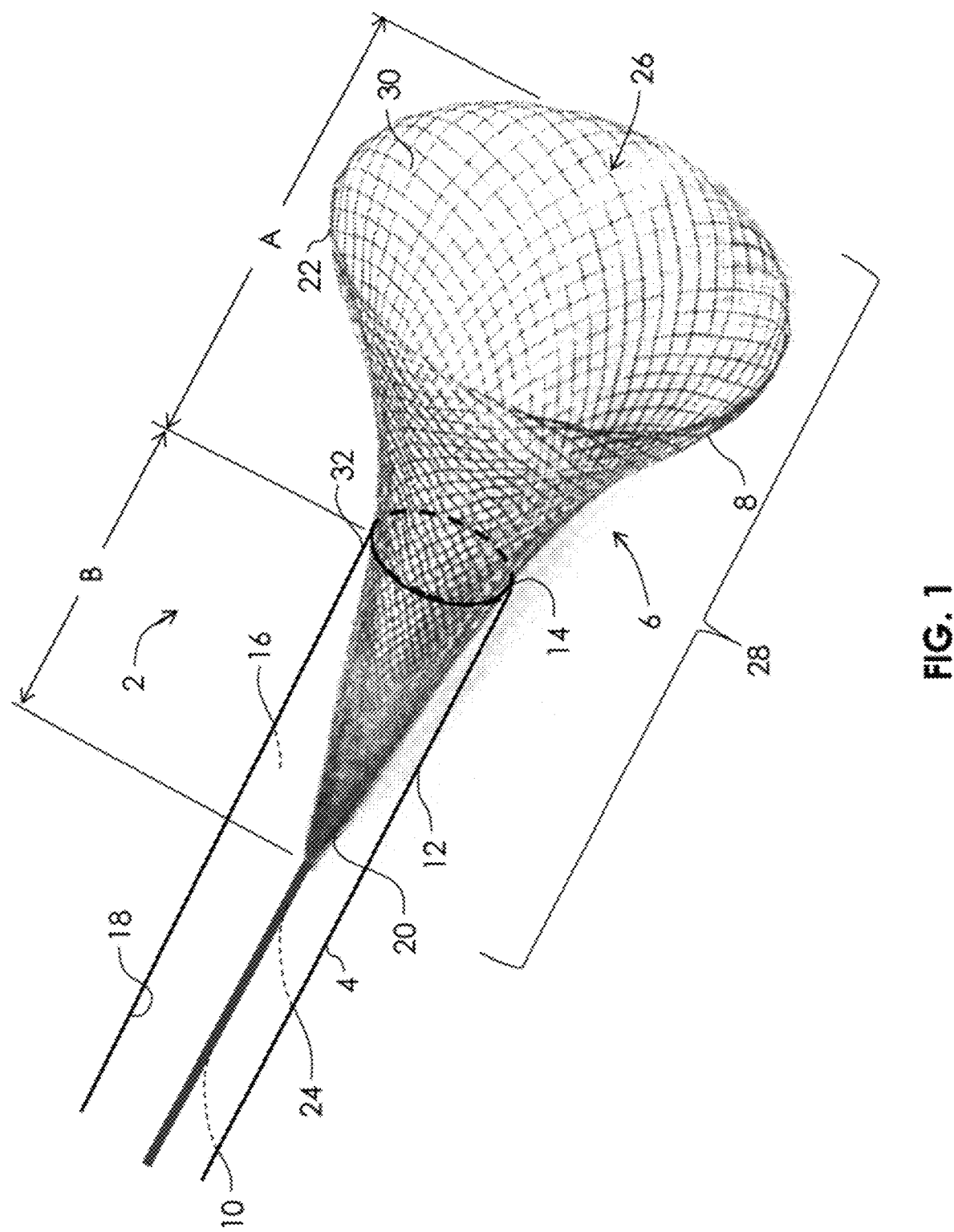
FIG. 1 is a perspective view of an embodiment of a delivery system for use with devices for treatment of a patient's vasculature.
Figure 1A:
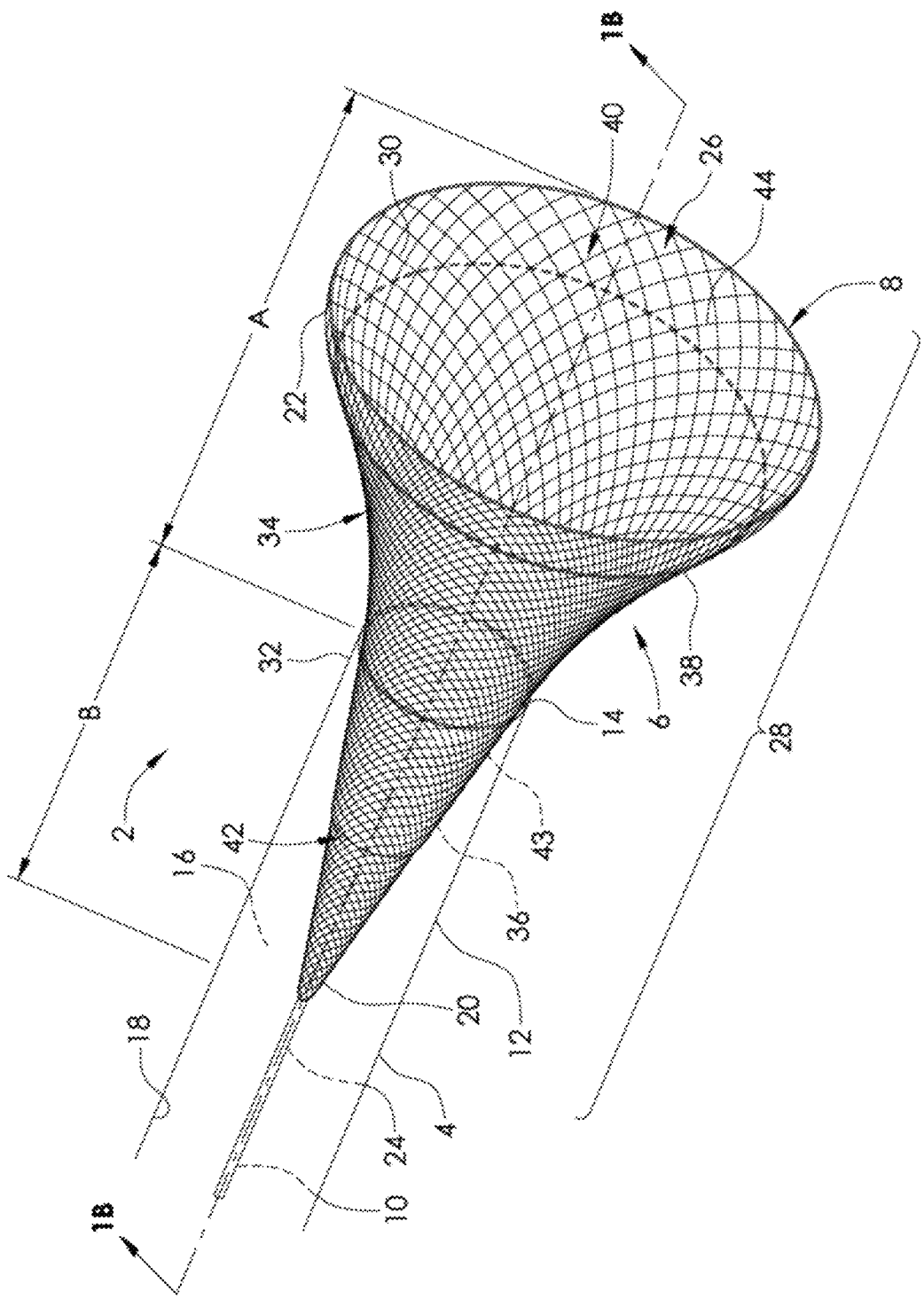
FIG. 1A is a perspective view of an embodiment of a delivery system and a mesh therapeutic device (stent or flow diversion device) within an elongate tubular member.

FIG. 1 illustrates a delivery system 2 comprising a microcatheter 4 and a delivery device 6. FIG. 1A illustrates a delivery system 2 comprising a microcatheter 4, a delivery device 6, and a mesh therapeutic device 34, such as a stent or a flow diversion device. The microcatheter 4 comprises an elongate tubular structure 12 having a wall 14, and having a lumen 16 extending therethrough. The microcatheter 4 may comprise a single extrusion, or may be of a composite construction comprising a plurality of layers. For example, a braided and/or coil-reinforced or otherwise reinforced construction may be sandwiched between an outer polymeric layer and an inner polymeric layer. The construction of the microcatheter 4 may change along its length, such that the distal end has a greater degree of flexibility than the proximal end. A middle portion may have an intermediate degree of flexibility relative to the proximal and distal ends. The inner surface 18 of the microcatheter 4 may be constructed from a lubricious material, such as polyethylene, ETFE (ethylene tetrafluoroethylene) or PTFE (polytetrafluoro ethylene). The inner surface 18 of the microcatheter may also, or alternatively, be coated with a lubricious material such as silicone to increase lubricity.

The delivery device 6 may comprise a self-expandable portion 8 and an elongate support member 10. The self-expandable portion 8 has a proximal end 20 and a distal end 22 and the elongate support member 10 has a proximal end (not shown) and a distal end 24. The proximal end 20 of the self-expandable portion 8 may be coupled at or near the distal end 24 of the elongate support member 10. The self-expandable portion 8 may comprise a tubular mesh structure (e.g., braided, woven, etc.) having a distal opening 26. In some embodiments, the tubular mesh may be a braided tube which is formed from filaments 30 comprising shape memory alloy, such as Nitinol (nickel-titanium). The filaments of the self-expandable portion 8 may have a diameter of between about 0.0010 inches and 0.0030 inches, alternatively between about 0.0010 inches and 0.0020 inches, alternatively between about 0.0013 inches and 0.0020 inches, alternatively between about 0.0013 inches and 0.0017 inches, alternatively between about 0.0015 inches and 0.0020 inches. The filaments may have a diameter of about 0.0010 inches, alternatively about 0.0013 inches, alternatively about 0.0015 inches, alternatively about 0.0017 inches, alternatively about 0.0018 inches, alternatively about 0.0020 inches. The self-expandable portion 8 of the delivery device 6 may be made from between 12 and 96 filaments, alternatively between 18 and 72 filaments, alternatively between 36 and 48 filaments, alternatively between 12 and 120, alternatively between 72 and 180, alternatively greater than 96 filaments. The self-expandable portion 8 of the delivery device 6 may be made from about 12, 18, 36, 48, 72, 96, 120, or 180 filaments.

Figure 3:
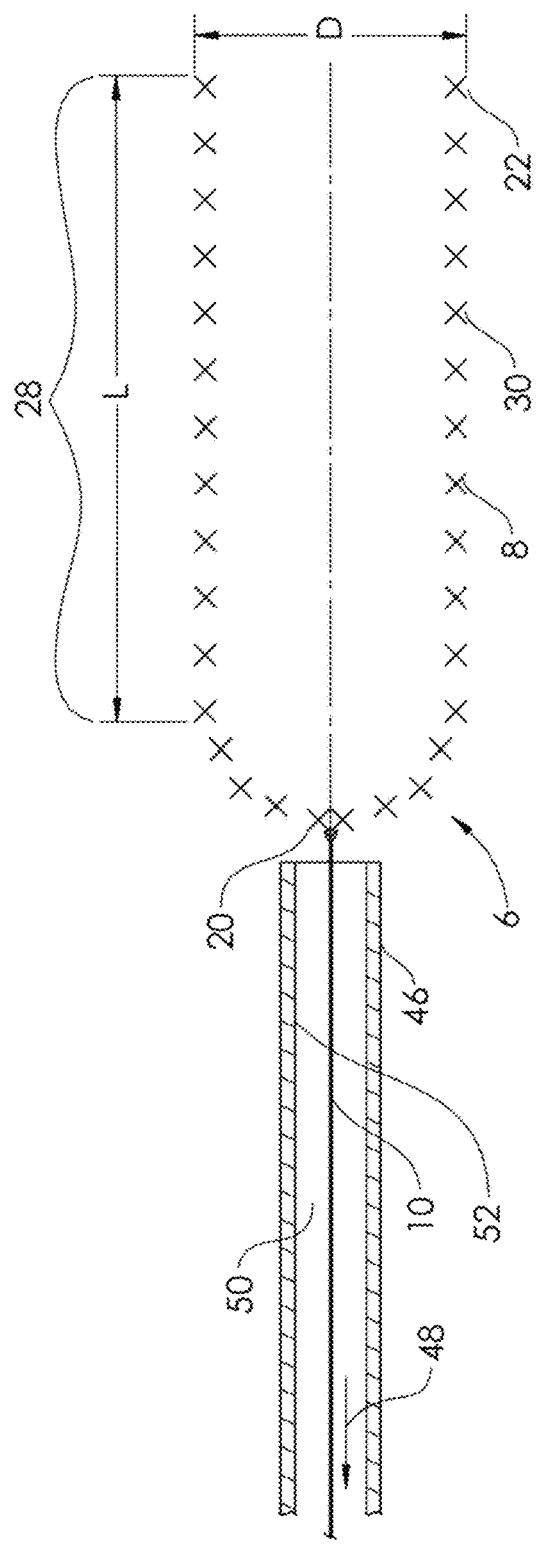
FIG. 3 is a sectional view of a delivery device in its expanded state prior to compression within an introducer sheath.

The tubular mesh of self-expandable portion 8 may be heat-formed to create an expanded state (FIG. 3). In the expanded state, a distal portion 28 has an expanded outer diameter D over a length L. The expanded outer diameter D of the self-expandable portion 8 may be about 2.0 mm to about 6.0 mm, alternatively about 3.0 mm to about 6.0 mm, alternatively about 3.5 mm to about 6.0 mm, alternatively about 4.0 mm to about 6.0 mm, alternatively about 4.5 mm to about 6.0 mm, alternatively about 5.0 mm to about 6.0 mm, alternatively about 3.5 mm to about 5.5 mm, alternatively about 4.0 mm to about 5.0 mm. The expanded outer diameter D of the self-expandable portion 8 may be about 2.0 mm, alternatively about 2.5 mm, alternatively about 3.0 mm, alternatively about 3.5 mm, alternatively about 4.0 mm, alternatively about 4.5 mm, alternatively about 5.0 mm, alternatively about 5.5 mm, alternatively about 6.0 mm. The length L of the section of the delivery device 6 having the expanded diameter may be about 2-15 mm, alternatively about 3-10 mm, alternatively about 3-5 mm. The length L of the section of the delivery device 6 having the expanded diameter may be about 2 mm, alternatively about 3 mm, alternatively about 4 mm, alternatively about 7 mm, alternatively about 10 mm. When the self-expandable portion 8 which has been heat-formed is allowed to self-expand (unconstrained) to its maximum diameter (e.g., expanded outer diameter D, as in FIG. 3) the expanded outer diameter D may be configured to have a substantially constant diameter along its length L (as shown), or may have a diameter that tapers along its length. For example, it may taper to an increasing diameter from proximal to distal, or may taper to an increasing diameter from distal to proximal. In some embodiments, it may have a maximum diameter in a center portion of its length, and taper down in diameter toward the distal end and toward the proximal end. In FIG. 1, the distal end 22 and portion A of the self-expandable portion 8 are able to self-expand more than portion B, which is constrained within the lumen 16 of the microcatheter 4. However, portion A is still not fully expanded, as the constriction caused by the microcatheter on portion B also affects the expansion of portion A, more so at a point near the distal end 32 of the microcatheter 4, than at the distal end 22 of the self-expandable portion 8.

Figure 2:
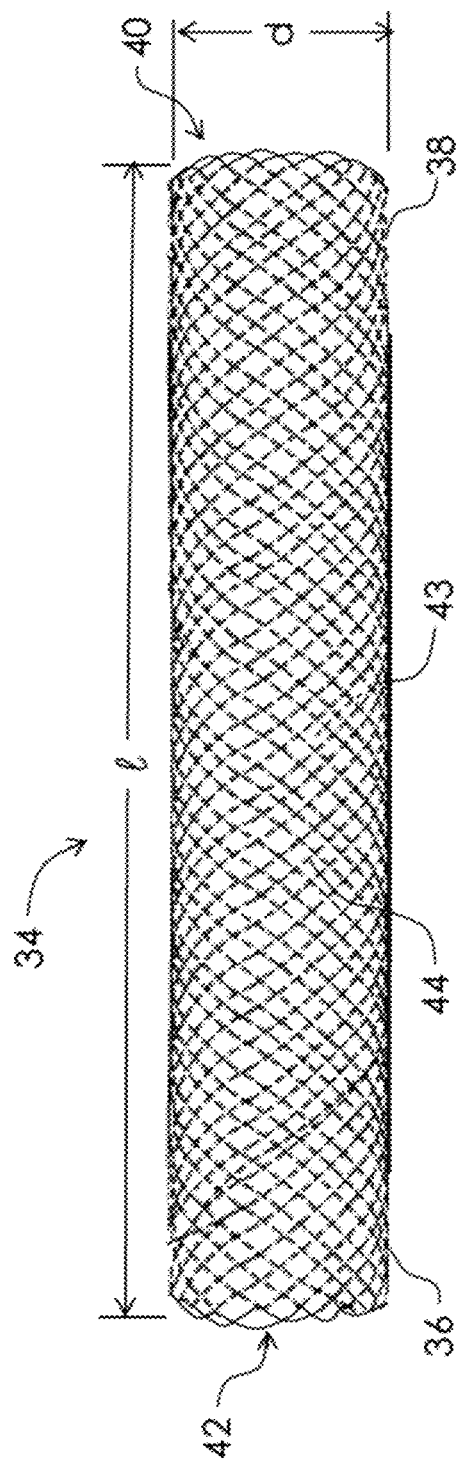
FIG. 2 is an elevation view of a mesh therapeutic device (stent or flow diversion device) for treatment of a patient's vasculature.

Turning to FIG. 2, a stent 34 having a proximal end 36 and a distal end 38 is shown. The term "stent" is intended to broadly describe a generally tubular or partially tubular structure which may be configured to engage the wall of a body lumen or duct of a patient, such as an artery or vein. "Stent" may describe a flow diversion device, such as a flow diversion device configured to extend within an artery at the site of an aneurysm. "Stent" may also describe a support lattice, such as stents used in angioplasty procedures. The stent 34 may be completely self-expanding (reach its desired target diameter without aid), partially self-expanding (reach an increased diameter by self-expanding, but then reach its desired target diameter by forced expansion, such as expansion from the delivery device 6 described herein or a balloon placed within its interior), or may be configured to be expandable (e.g., expandable using the delivery device 6 described herein or a balloon). The stent 34 may comprise a tubular mesh structure (e.g., braided, woven, etc.) formed of a filaments 44 and having a distal opening 40, a proximal opening 42, and a lumen 43 extending therebetween. In some embodiments, the tubular mesh may be a braided tube which is formed from filaments 44 comprising a shape memory alloy, such as Nitinol (nickel-titanium). The stent 34 in FIG. 2 is shown in its self-expanded condition (unconstrained), and in this self-expanded condition has a self-expanded inner diameter d. The self-expandable portion 8 of delivery device 6 is configured to engage the stent from within the lumen 43. For purposes of delivering the stent 34 into a vessel (e.g., artery) using the delivery device 6, the expanded outer diameter D of the self-expandable portion 8 should be greater than or equal to the self-expanded inner diameter d of the stent 34, stated by the equation:

$$D \geq d$$

In some embodiments, the self-expanded inner diameter d of the stent 34 may be between about 2 mm and about 5 mm, or between about 3 mm and about 4 mm. The self-expanded inner diameter d of the stent 34 may also be about 2.0 mm, alternatively about 2.5 mm, alternatively about 3.0 mm, alternatively about 3.5 mm, alternatively about 4.0 mm, alternatively about 4.5 mm, alternatively about 5.0 mm, alternatively about 5.5 mm, alternatively about 6.0 mm. Stent 34 may have a total length of approximately 4 mm, alternatively about 5 mm, alternatively about 6 mm, alternatively about 10 mm, alternatively about 15 mm. In some cases, the self-expanded inner diameter d of the stent 34 may be tapered. For example, the stent 34 may be configured to extend in an artery that itself tapers, e.g., decreasing in diameter from proximal to distal. In some embodiments, the self-expanded inner diameter d may increase a total of between about 0.5 mm and about 2.0 mm over the length 1 of the stent 34. In some embodiments, the self-expanded inner diameter d may increase a total of between about 1.0 mm and about 1.5 mm over the length 1 of the stent 34. The expanded outer diameter D of the self-expandable portion 8 of delivery device 6 may also taper over its length in order to better mechanically engage with a tapered self-expanded inner diameter d of the stent 34. In some embodiments, the expanded outer diameter D of the self-expandable portion 8 of delivery device 6 may stay generally constant, even though it is configured to mechanically engage with a tapered self-expanded inner diameter d of the stent 34. For example, the self-expanded inner diameter d of the stent 34 may taper between 3.0 mm and 3.5 mm, and the expanded outer diameter D of the self-expandable portion 8 of delivery device 6 may stay constant at 3.75 mm. When it is engaged with the 3.0 mm to 3.5 mm inner diameter of the stent 34, the 3.75 mm expanded outer diameter D may be semi-constricted, so that it conforms to the tapered inner diameter of the stent 34.

The filaments of the stent 34 may have a diameter of between about 0.0010 inches and 0.0030 inches, alternatively between about 0.0010 inches and 0.0020 inches, alternatively between about 0.0013 inches and 0.0020 inches, alternatively between about 0.0013 inches and 0.0017 inches, alternatively between about 0.0015 inches and 0.0020 inches. The filaments may have a diameter of about 0.0010 inches, alternatively about 0.0013 inches, alternatively about 0.0015 inches, alternatively about 0.0017 inches, alternatively about 0.0018 inches, alternatively about 0.0020 inches. The self-expandable portion 8 of the delivery device 6 may be made from between 36 and 144 filaments, alternatively between 48 and 108 filaments, alternatively between 48 and 96 filaments, alternatively between 72 and 96 filaments. The self-expandable portion 8 of the delivery device 6 may be made from about 36, 48, 72, 96, or 108 filaments. The total number of filaments in the stent may be about 2.0 to about 5 times, alternatively about 2.5 to about 4.25 times, alternatively about 2.6 to about 4.05 times, alternatively about 2.5 times to about 4.0 times, alternatively about 2.0 times to about 4.0 times, alternatively about 2.0 times to about 3.5 times more than the number of filaments in the self-expandable portion 8 of the delivery device 6.

Figure 1B:
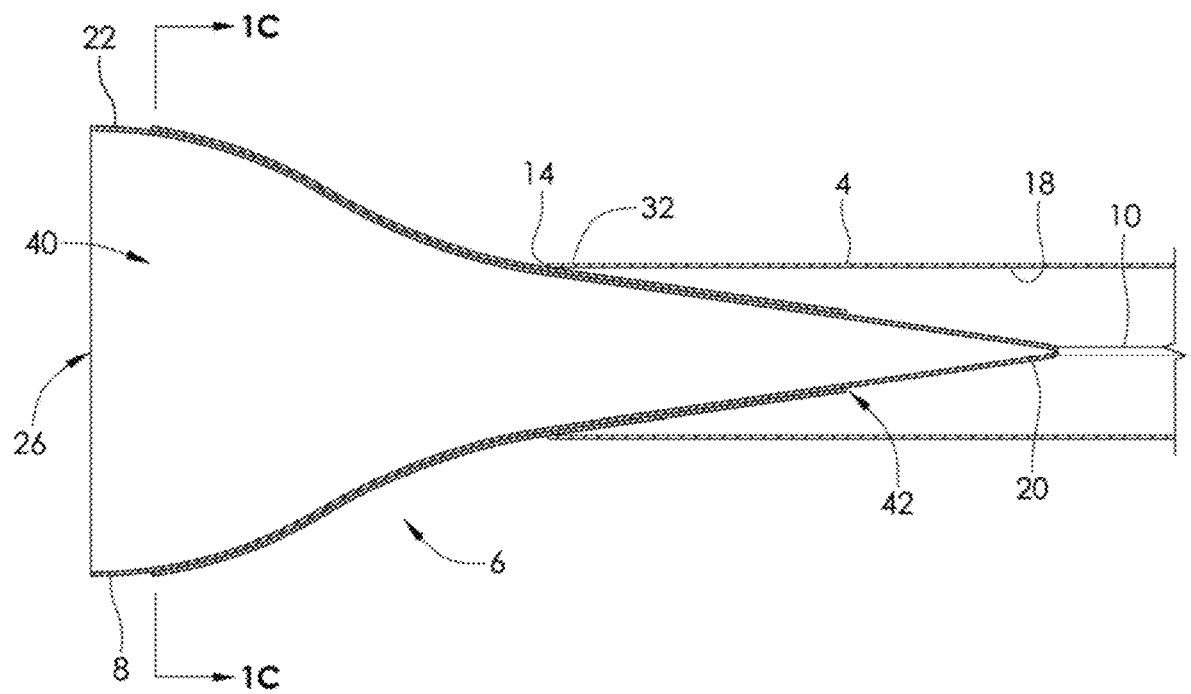
FIG. 1B is a sectional view of FIG. 1A along plane 1B.
Figure 1C:
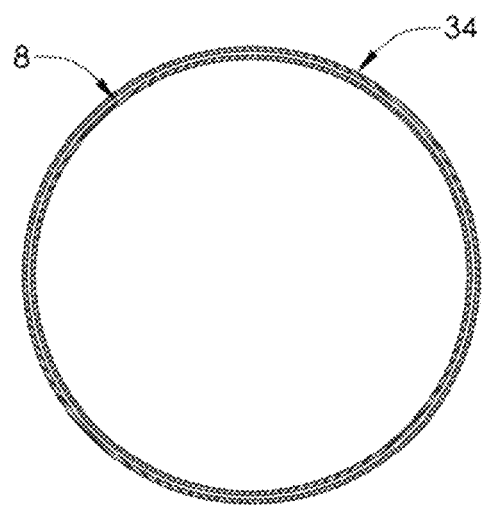
FIG. 1C is a sectional view of FIG. 1B along plane 1C.

As illustrated in FIGS. 1A-1C, the stent 34 is engaged with the self-expandable portion 8 of the delivery device 6. The inner surface of the stent 34 is in contact with the outer surface of the self-expandable portion 8 of the delivery device 6. The inner surface of the stent 34 may be engaged with the outer surface of the self-expandable portion 8 of the delivery device 6, for example, through mechanical engagement, frictional engagement, or intermeshing. The inner surface of the stent 34 may be engaged to at least a portion of the outer surface of the self-expandable portion 8 of the delivery device 6 substantially from the proximal end to the distal end of the stent, which allows for improved control, placement, and delivery of the stent at the target site.

Prior to loading the delivery device 6 and stent 34 together in an introducer sheath 46 (FIGS. 3-9), the delivery device 6 and stent 34 may be mechanically engaged to each other. Mechanical engagement may in some cases be due predominantly to friction between the stent 34 and the self-expandable portion 8 of delivery device 6, or may be due predominantly to intermeshing between the stent 34 and the self-expandable portion 8 of delivery device 6. Mechanical engagement may also in some cases be due to a combination of friction and intermeshing between the stent 34 and the self-expandable portion 8 of delivery device 6. Intermeshing may include "keying" between filaments 30 of the self-expandable portion 8 of delivery device 6 and filaments 44 (or struts) of the stent 34. The intermeshing may be predominantly along a particular axis or may be along several axes. In some embodiments, the filaments 30 of the self-expandable portion 8 of delivery device 6 and filaments 44 of the stent 34 may be configured to match or register with each other, either by having similar or identical dimensions (diameters, thicknesses) or by being braided or woven with similar or identical dimensions (pics or crossings per unit dimension) or patterns (one filament over one filament, two filaments over two filaments, two filaments over one filament, etc.). In other embodiments, it may be desired to provide a stent 34 and a self-expandable portion 8 that do not match each other, for example, wherein they are mechanically different from each other. In cases wherein it is desired to have a self-expandable portion 8 that is relatively stiffer than the stent 34 (e.g., axial stiffness and/or radial stiffness), the stent 34 and the self-expandable portion 8 may be constructed differently from each other. For example, the braid angle of the stent may be different from the braid angle of the self-expandable portion 8 and/or the filament diameter of the stent 34 may be different from the filament diameter of the self-expandable portion 8. The braid angle of the self-expandable portion 8 of the delivery device 6 may be between about 70° and about 85°, alternatively between about 73° and about 82°, alternatively between about 75° and about 80°. The braid angle of the stent 34 may be between about 70° and about 85°, alternatively between about 73° and about 82°, alternatively between about 75° and about 80°. The degree of mechanical engagement may be controlled by configuring the self-expandable portion 8 and the stent 34 such that an axial force F (FIG. 6) applied to an external portion of the stent 34 can be allowed to reach a critical level without any disruption (e.g., relative axial displacement) between the self-expandable portion 8 and the stent 34. This critical level may be about 227 grams$_f$ (0.5 pounds$_f$) or greater, 454 grams$_f$ (1.0 pounds$_f$) or greater, or 2,270 grams$_f$ (5.0 pounds$_f$) or greater. This critical level may also be about 227 grams$_f$ (0.5 pounds$_f$) to about 4,540 grams$_f$ (10.0 pounds$_f$), alternatively about 454 grams$_f$ (1.0 pounds$_f$) to about 2,270 gram Sf (5.0 pounds$_f$). The axial force F at which the stent 34 becomes separated from the self-expandable portion 8 may be referred to as the separation force.

Figure 4:
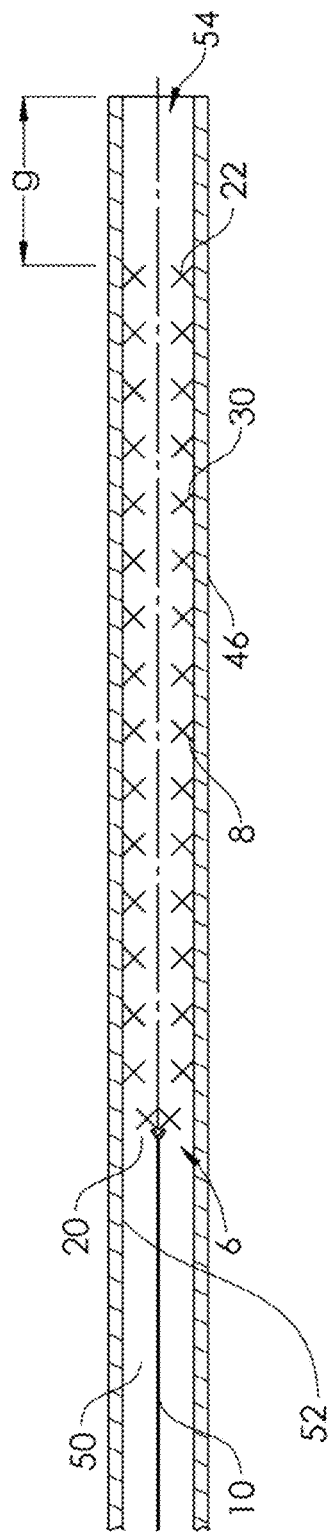
FIG. 4 is a sectional view of the delivery device of FIG. 3 in an at least partially compressed state within an introducer sheath.

FIGS. 3-9 illustrate a method for preparing a stent 34 for delivery via a delivery device 6, from within an introducer sheath 46. In FIG. 3, the elongate support member 10 is backloaded (arrow 48) through lumen 50 of the introducer 46 sheath. When the proximal end (not shown) of the elongate support member 10 exits the proximal end (not shown) of the introducer sheath 46, elongate support member 10 exits the proximal end (not shown) of the introducer sheath 46, a tension T is placed on the elongate support member (at its proximal end), while also holding the introducer sheath 46, and the self-expandable portion 8 is pulled into the lumen 50 of the introducer sheath 46 and is constricted by the inner surface 52 of the introducer sheath 46 (FIG. 4). It may be desired to leave a gap g between the distal opening 54 of the introducer sheath 46 and the distal end 22 of the self-expandable portion 8. The dimension of the gap g may be chosen in order to aid longitudinal alignment with the self-expandable portion 8 with the stent 34.

Figure 5:
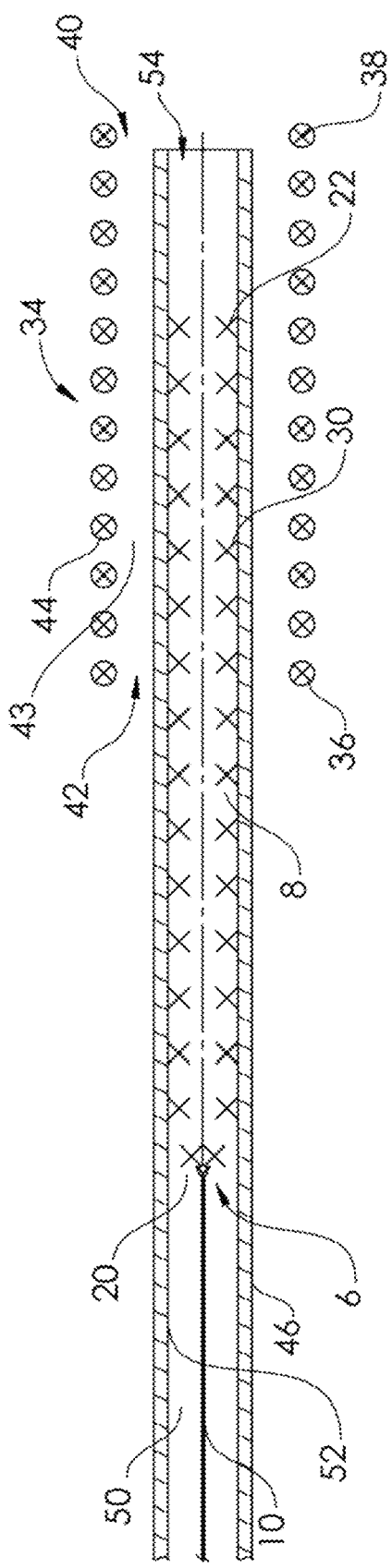
FIG. 5 is a sectional view of the delivery device in its compressed state within the introducer sheath and a mesh therapeutic device in its expanded state.

Prior to loading the stent and delivery device into the introducer sheath, the stent and the delivery device can be aligned in different ways. As seen in FIG. 5, by placing the stent 34 over the introducer sheath 46 at a particular longitudinal position, the stent 34 may be longitudinally aligned, for example, either with the self-expandable portion 8, or with the distal opening 54 (i.e., distal end) of the introducer sheath (or both). The distal end 38 of the sheath 34 may be the portion aligned, or the proximal end 36 of the sheath 34 may be the portion aligned. Alternatively, the proximal end 36 of the sheath 36 may be aligned with the proximal end 20 of the self-expandable portion 8. In some embodiments, it may be desired to longitudinally center the length 1 of the stent 34 along the length L of the distal portion 28 of the self-expandable portion 8. In some embodiments, it may be desired to skew or shift the length 1 of the stent 34 in relation to the length L of the distal portion 28 of the self-expandable portion 8, either skewed distally or skewed proximally.

Figure 6:
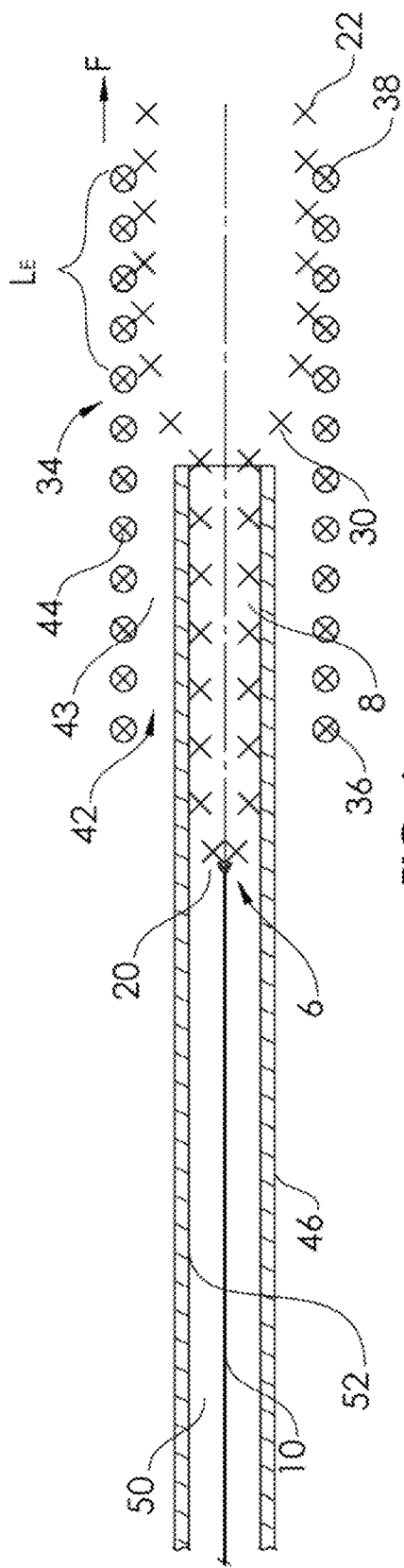
FIG. 6 is a sectional view of the delivery device and the mesh therapeutic device being coupled together in longitudinal alignment.

The self-expandable portion 8 of the delivery device 6 must engage the stent 34 before loading both the delivery device and stent into the introducer sheath 46. In FIG. 6, the self-expandable portion 8 is shown being extended from the introducer sheath (e.g., by placing a compressive force on the proximal end of the elongate support member 10) such that the filaments 30 of the self-expandable portion 8 mechanically engage the filaments 44 of the stent 34 over an engagement length LE. As the self-expandable portion 8 is further extended, the engagement length LE increases, and the mechanical engagement (e.g., axial decoupling force) increases accordingly. In FIG. 7, the engagement length LE is at its maximum, as the stent 34 and the distal portion 28 of the self-expandable portion 8 are fully outside the lumen 50 of the introducer sheath 46.

There are numerous possible ways to load the stent 34 and delivery device 6 into the introducer sheath 46. In order to load the stent 34 and the self-expandable portion 8 of delivery device 6 together into the lumen 50 of the introducer sheath 46, an assembler may manipulate the stent 34 and the self-expandable portion 8 using fingers 56, 58, for example, first finger 56 and thumb 58 (FIG. 8). In some cases, the fingers 56, 58 are used to pinch or squeeze the stent 34 and the self-expandable portion 8 to decrease their total diameter at the distal opening 54 of the introducer sheath 46 so that they are able to be inserted within the lumen 50. Tension T (traction) may be applied on the proximal end of the elongate support member 10 while holding the proximal end of the introducer sheath 46 to further aid the insertion of the stent 34 and the self-expandable portion 8 within the lumen 50.

Figure 9:
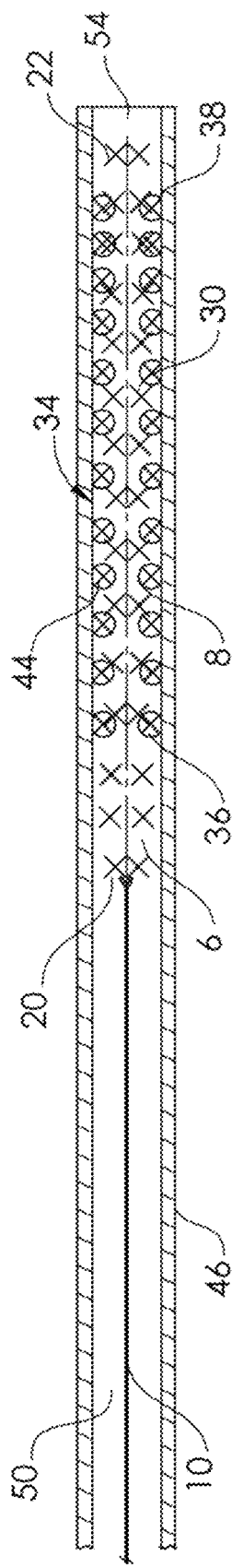
FIG. 9 is a sectional view of the delivery device and the mesh therapeutic device positioned together completely within the introducer sheath.

An alternative technique to that of FIG. 8 is shown in FIG. 8A. An insertion funnel 60 may be constructed by flaring a tube or by shrinking a shrink tube, in order to provide a small inner diameter 62 and an opposing large inner diameter 64, with a tapered inner diameter 66 communicating therebetween. The dimension of the small inner diameter 62 can be made to be equal to or slightly less than the inner diameter of the lumen 50 of the introducer sheath 46, thus allowing sliding insertion of the step-up 68 in outer diameter caused by the proximal end 36 of the stent 34. A joint member 70 serves to align the lumen 50 of the introducer sheath 46 with the small inner diameter 62 of the insertion funnel 60, and may be configured by shrinking a shrink tube over the introducer sheath 46 and the insertion funnel 60. The large inner diameter 64 can be made larger than the outer diameter of the stent 34, when it is engaged with the self-expandable portion 8, thus allowing for smooth insertion. This diameter may be larger than the unconstrained outer diameter of the stent 34. Once the entirety of the stent 34 and the self-expandable portion 8 are inserted within the lumen 50, the insertion funnel 60 and the joint member 70 may be removed. Yet another alternative to the technique of FIG. 8 is shown in FIG. 8B. The introducer sheath 46 includes a flare 72 having a large inner diameter 74. The dimension of the large inner diameter 74 can be larger than the outer diameter of the stent 34, when it is engaged with the self-expandable portion 8, thus allowing for smooth insertion. Once the entirety of the stent 34 and the self-expandable portion 8 are inserted within the lumen 50 and pulled back so that the most distal end of the stent 34 and/or self-expandable portion are sufficiently out of the way, the flare 72 may be cut from the introducer sheath, for example at a cutting point 76. Thus, this cutting point will create the new distal opening 54 of the introducer sheath 46. FIG. 9 illustrates the stent 34 and self-expandable portion 8 fully retracted into the lumen 50 of the introducer sheath 46. The configuration of FIG. 9 may represent the packaging configuration of the stent 34 and the delivery device 6. Alternatively, the configuration of FIG. 9 may represent the configuration of the stent 34 and the delivery device 6, after preparation by a user. FIGS. 3-9 may represent the steps performed by a supplier. Or FIGS. 3-9 may represent the steps performed by a user.

Figure 10:
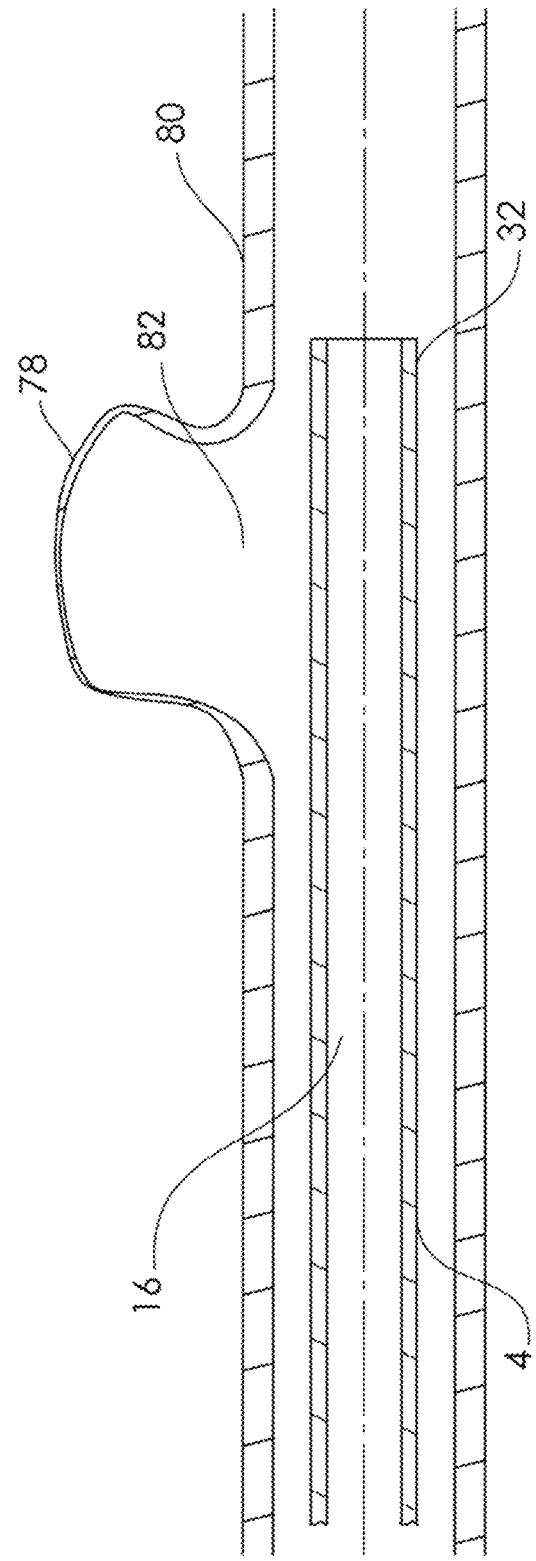
FIG. 10 is a sectional view of a microcatheter in position in proximity to a cerebral aneurysm.
Figure 11:
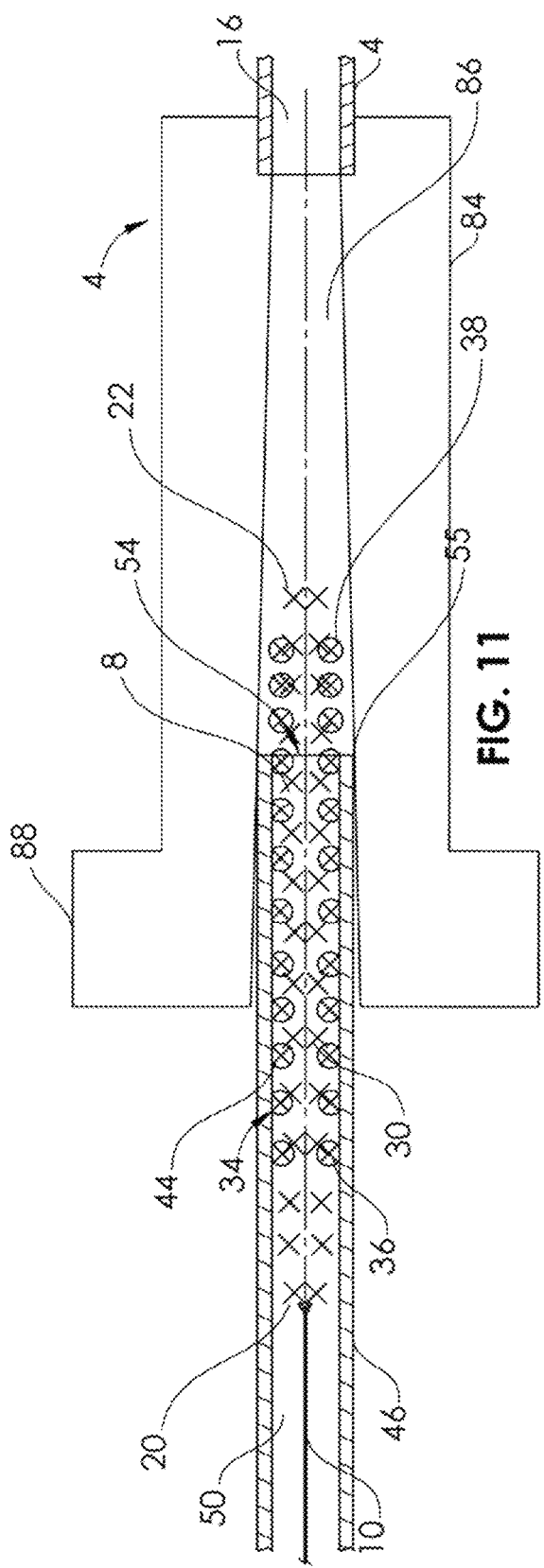
FIG. 11 is a sectional view of the delivery device and the mesh therapeutic device being delivered from the introducer sheath into a hub at the proximal end of a microcatheter.

FIGS. 10-17 illustrate a delivery system 2 comprising a microcatheter 4 and a delivery device 6 in use for delivering a stent 34 (e.g., flow diversion device) across the neck 82 of an aneurysm 78 of an artery 80. In FIG. 10 a user inserts a microcatheter 4 into the vascular system of a patient, and tracks the microcatheter 4 such that the distal tip 32 of the microcatheter 4 is located in a position adjacent the neck 82 of the aneurysm 78. The microcatheter 4 may be inserted through a guiding catheter, which has been inserted through an introducer (e.g., valved introducer), which itself has been inserted into a peripheral access artery (femoral artery, brachial artery, radial artery, etc.), or even directly into a carotid artery. In FIG. 10, the distal tip 32 of the microcatheter 4 has been placed (or tracked) to a position just distal to the neck 82 of the aneurysm 78. With the microcatheter 4 in a desired position adjacent the neck 82 of the aneurysm 78, the stent 34 and the self-expandable portion 8 of the delivery device 6 are inserted together into the lumen 16 of the microcatheter 4, through the introducer sheath 46 (FIG. 11). With the stent 34 and the self-expandable portion 8 still completely retracted within the lumen 50 of the introducer sheath 46, the distal end 55 of the introducer sheath 46 is inserted into a cavity 86 within a hub 84 which is coupled to the microcatheter 4. The cavity 86 is coextensive with the lumen 16 of the microcatheter 4. The cavity 86 may comprise a luer taper and may include an interface (e.g., bump, groove) for interfacing with the distal end 55 of the introducer sheath 46. With the distal end 55 of the introducer sheath in position within the cavity 86, the distal opening 54 of the introducer sheath 46 empties into the cavity 86, thus allowing smooth, direct insertion of the stent 34 and the self-expandable portion 8 of delivery device 6 into the cavity 86 and into the lumen 16 of the microcatheter 4. The hub 84 may include a luer lock 88, for coupling to a syringe or to other luer connectors. In FIG. 11, the stent 34 and the self-expandable portion 8 are shown being inserted into the cavity 86, as the user applied an insertion force (compression) on the proximal end of the support member 10. After the stent 34 and the self-expandable portion 8 have been completely inserted into the lumen 16 of the microcatheter 4, and in some cases, after a proximal, stiff portion of the support member 10 has also been inserted into the lumen of the microcatheter 4, the introducer sheath 46 may be removed proximally, while holding the support member 10 distal of the introducer sheath 46.

Figure 12:
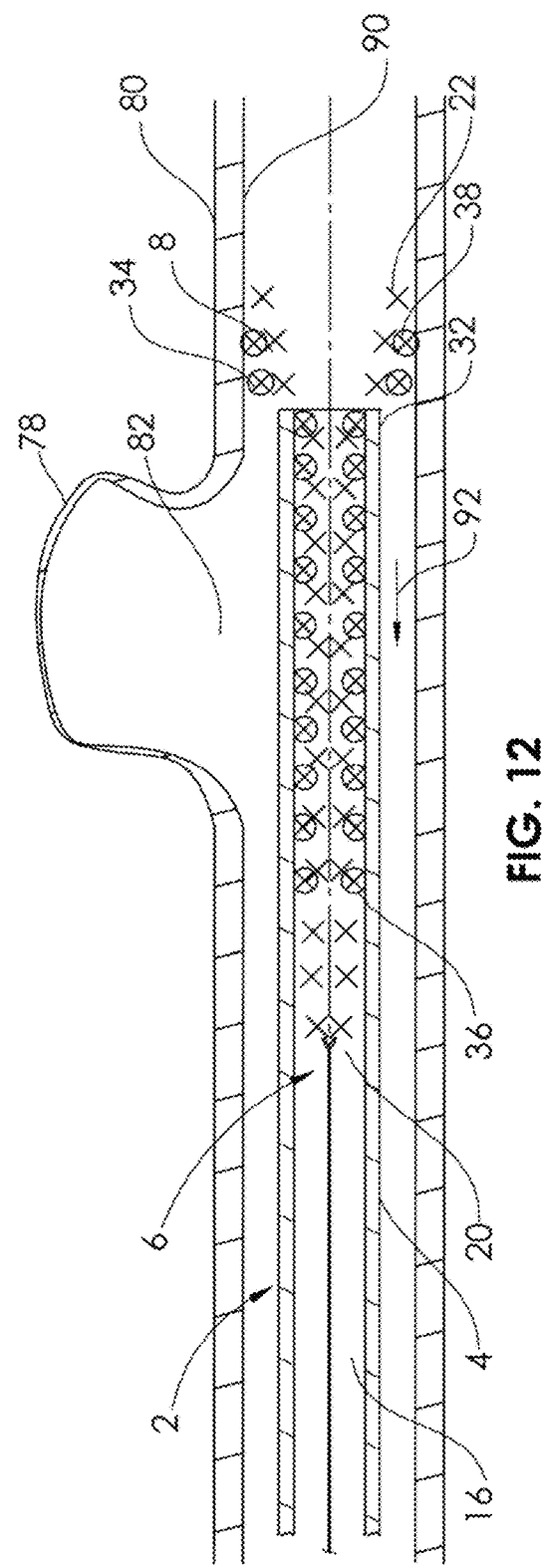
FIG. 12 is a sectional view of the mesh therapeutic device being delivered by the delivery device from the distal end of a microcatheter adjacent the cerebral aneurysm.

Now, the user is able to continue inserting the delivery device 6 by pushing on the proximal end of the support member 10 until, as shown in FIG. 12, the stent 34 begins to self-expand against the inner wall 90 of the artery 80. In addition, the self-expansive action of the self-expandable portion 8 of the delivery device 6 may further expand the stent 34 (e.g., increase its diameter further and/or increase the radial force it applies against the inner wall 90 of the artery 80). The microcatheter 4 may be pulled proximally (arrow 92) while the support member 10 of the delivery device 6 is held substantially static (via a compressive force applied to its proximal end) so as to deliver the stent 34 in place across the neck 82 of the aneurysm 78.

Prior to and during the delivery of the devices the user may view the delivery of the stent 34 and the self-expandable portion by use of angiography or fluoroscopy or other imaging modalities. Radiopaque marker bands may be located on the distal end 32 of the microcatheter 4 and at one or more locations on the stent 34 and/or the self-expandable portion 8. In addition, or alternatively, the materials (e.g., filaments) of the stent 34 and/or the self-expandable portion 8 may include radiopaque materials (platinum, platinum/tungsten, platinum/iridium, gold, etc.) so that they may be visualized in angiography or fluoroscopy. In some embodiments, the filaments may comprise drawn filled tubes (DFT), such as those supplied by Fort Wayne Metals, Fort Wayne, Ind., USA. Such DFT filaments may comprises an outer shell of nickel-titanium and an inner core of platinum. In other embodiments, the filaments may comprise cobalt-chromium alloys or platinum-tungsten alloys. The outer diameter may range from about 0.0004 inches to 0.005 inches or from about 0.00075 inches to about 0.003 inches. The filaments may comprise a mixture of multiple different filament diameters or thicknesses and/or a mixture of different filament materials.

Figure 13:
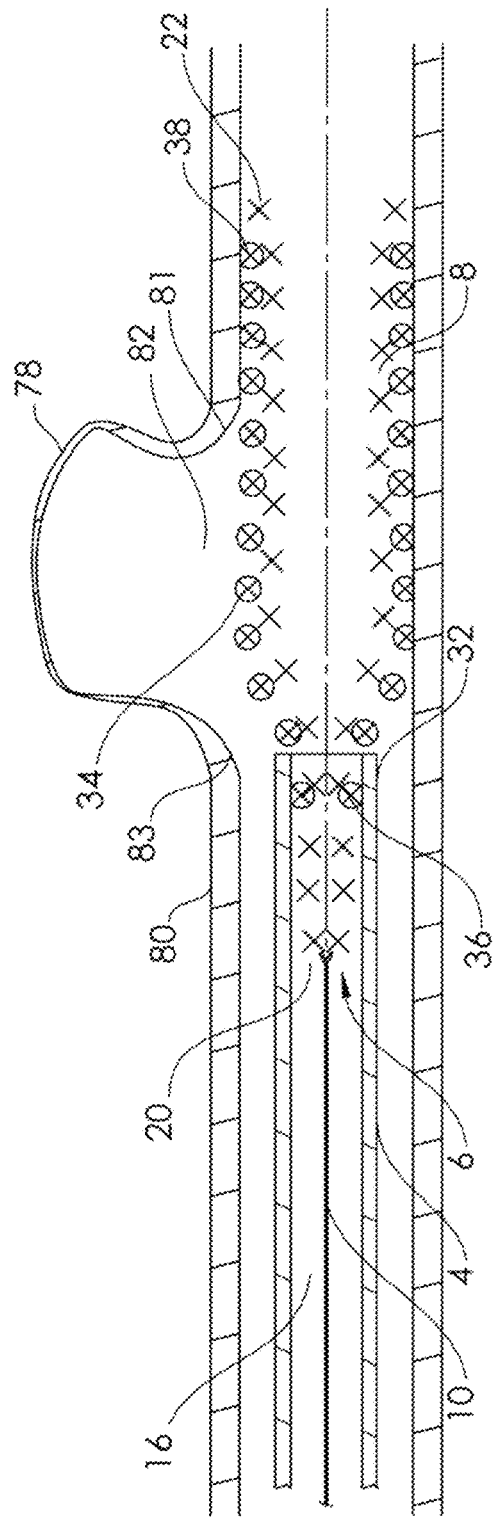
FIG. 13 is a sectional view of the mesh therapeutic device partially delivered in an undesired position or configuration.
Figure 14:
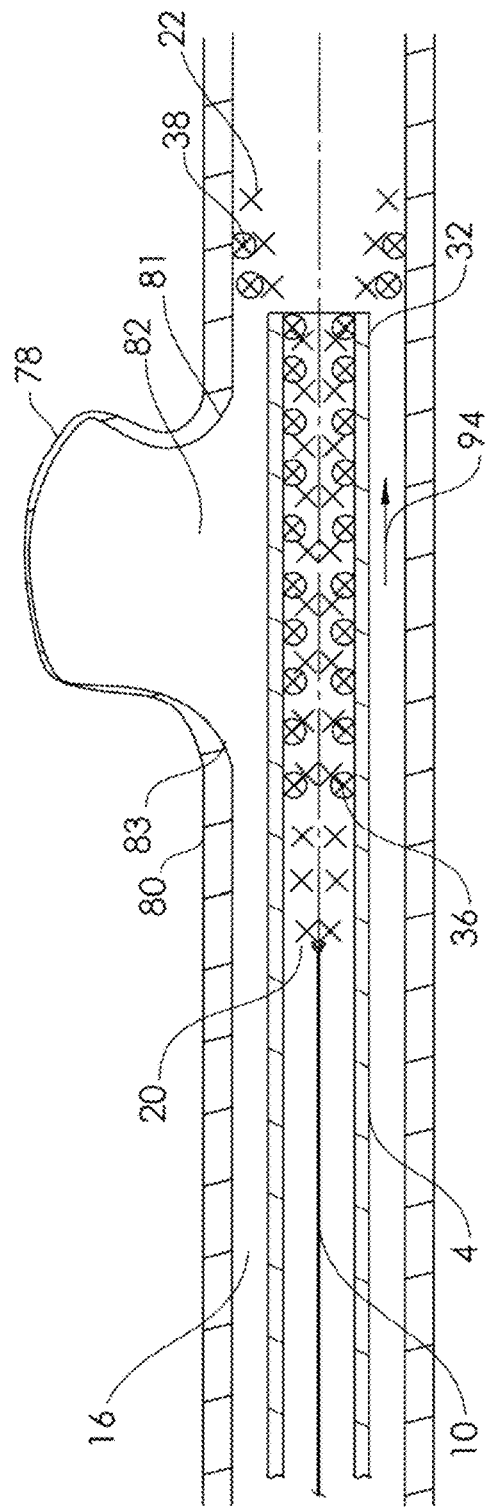
FIG. 14 is a sectional view of the mesh therapeutic device being retracted by the delivery device into the microcatheter.

As shown in FIG. 13, in some cases, a user may discover, while delivering the stent 34, that the stent 34 is about to be delivered in an undesirable location or position, for example, in relation to the neck 82 of the aneurysm 78. For example, in FIG. 13, the longitudinal distance between the distal end 38 of the stent 34 and a distal extremity 81 of the neck 82 may appear to be significantly greater than the longitudinal distance between the proximal end 36 of the stent 34 and a proximal extremity 83 of the neck 82, if the stent 34 gets fully delivered. The user may determine that this is undesired, and thus has the ability to advance the microcatheter 4 (FIG. 14, arrow 94) while maintaining traction on the support member 10, in order to recapture or recompress the stent 34 and the self-expandable portion 8 back within the lumen 16 of the microcatheter 4. The mechanical engagement between the stent 34 and the self-expandable portion 8, as described herein, allows the stent 34 to be delivered and to be retracted one-to-one (1:1) with the delivery device 6, without any significant kinking, buckling, or stretching. The frictional and/or longitudinal engagement forces are distributed along the length of the stent 34, both in the constricted configuration (inside the lumen 16) and in the expanded configuration (e.g., FIG. 13), thus avoiding kink points or stress concentrations that may cause kinking, buckling, or stretching. The distribution of the frictional and/or longitudinal engagement forces along the length of the stent 34 also allows for one-to-one (1:1) movement of the stent with the delivery device, i.e., for every 1.0 mm that the delivery device is advanced, the stent will also be advanced 1.0 mm.

Figure 15:
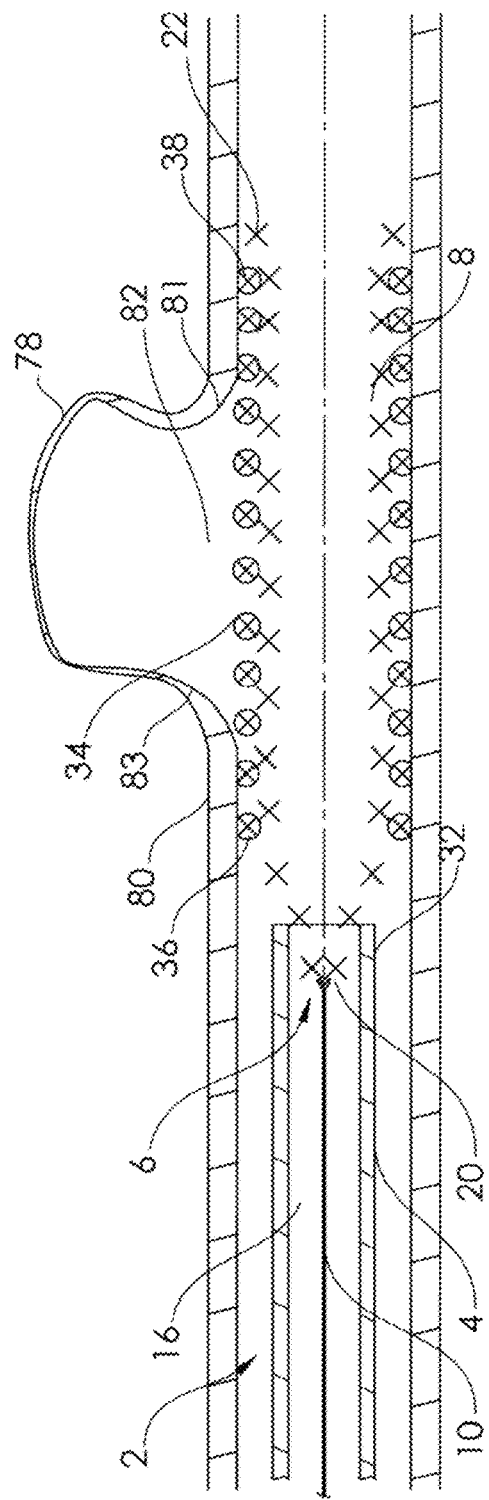
FIG. 15 is a sectional view of the mesh therapeutic device fully delivered in a desired position and configuration spanning the cerebral aneurysm.
Figure 16:
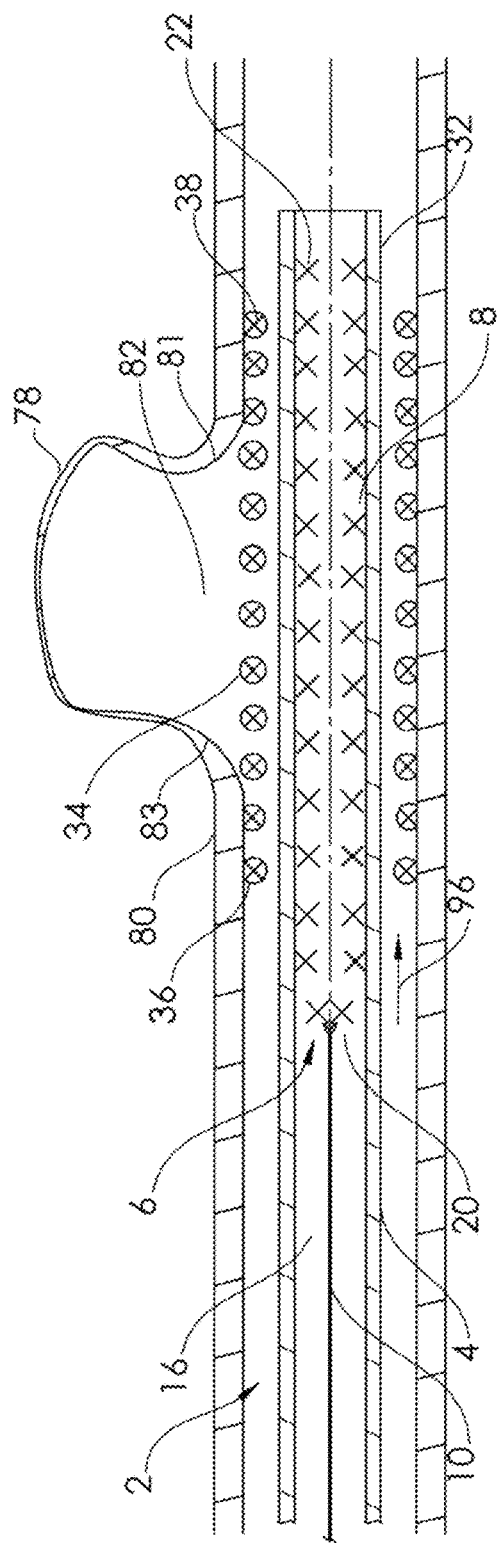
FIG. 16 is a sectional view of the delivery device compressed by the microcatheter, with the mesh therapeutic device remaining in position spanning the cerebral aneurysm.
Figure 17:
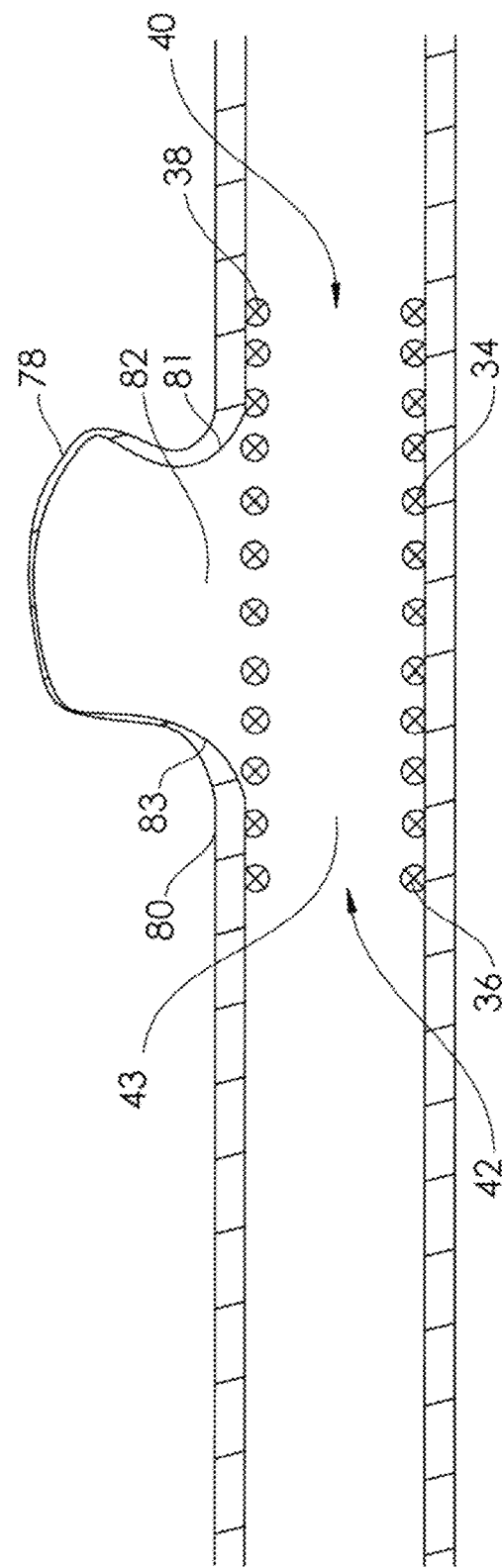
FIG. 17 is a sectional view of the mesh therapeutic device in position spanning the cerebral aneurysm, with the delivery device and microcatheter retracted or removed.

After retracting the stent 34 and the self-expandable portion 8 back into the lumen 16 of the microcatheter 4, the microcatheter 4 can be repositioned, and the stent 34 can be redelivered, as shown in FIG. 15. The user may prefer the positioning depicted in FIG. 15 because the stent 34 is relatively evenly positioned longitudinally in relation to the neck 82 of the aneurysm 78, with the longitudinal distance between the distal end 38 of the stent 34 and a distal extremity 81 of the neck 82 generally comparable to the longitudinal distance between the proximal end 36 of the stent 34 and a proximal extremity 83 of the neck 82. Once the user is satisfied with the position of the stent 34, the user may then advance the microcatheter 4 (FIG. 16, arrow 96) while applying traction to the proximal end of the support member 10. Because the end 36 of the stent 34 is outside of the lumen 16 of the microcatheter 4 (FIG. 15) when the stent is fully deployed, the advancement of the microcatheter 4 as in FIG. 16 causes only the self-expandable portion 8 to be constrained within the lumen 16 of the microcatheter, leaving the stent 34 in place within the artery 80, across the neck 82 of the aneurysm. The microcatheter 4 and the delivery device 6 may now be removed, leaving the stent 34 in place (FIG. 17). The inner lumen 43 of the stent 34 may now allow blood flow through the artery 80, and the filaments 44 of the stent 34 may limit a significant amount of blood from entering the aneurysm 78, thus allowing stagnation of blood flow within the aneurysm 78 and thrombosis.

Figure 18:
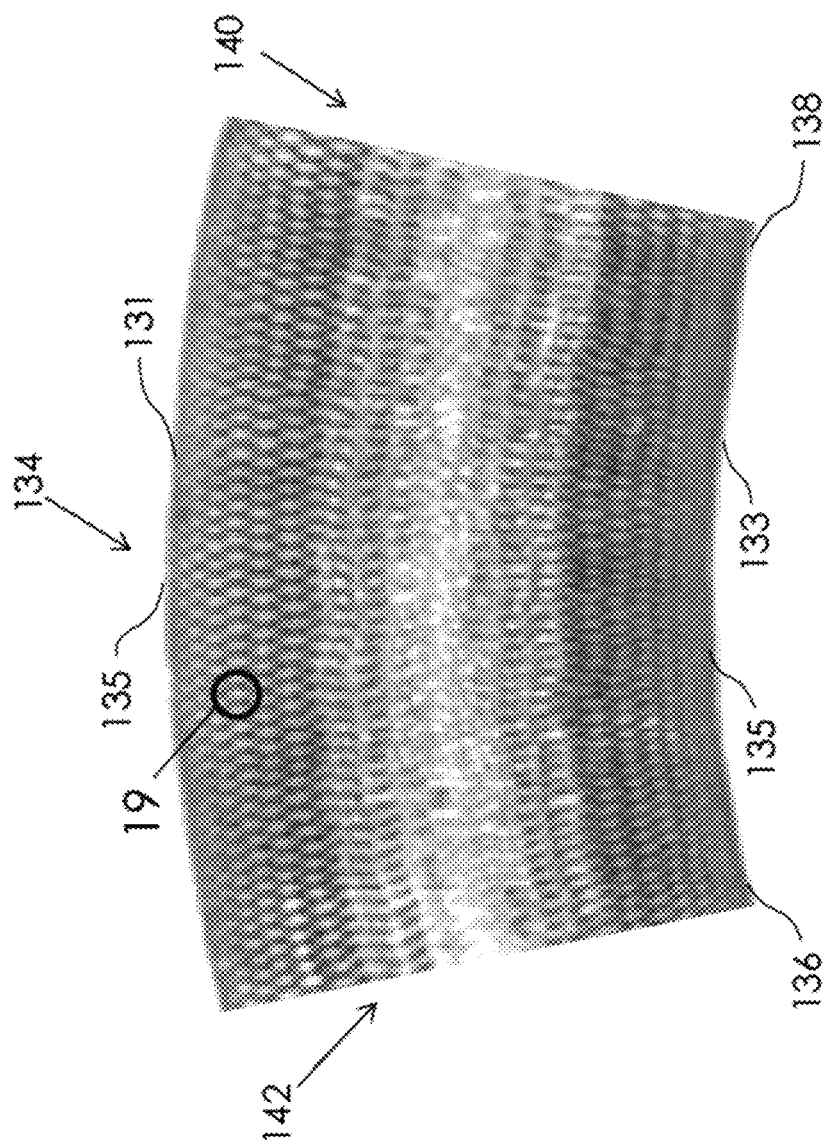
FIG. 18 is a side view of a mesh therapeutic device in a curved condition.
Figure 19:
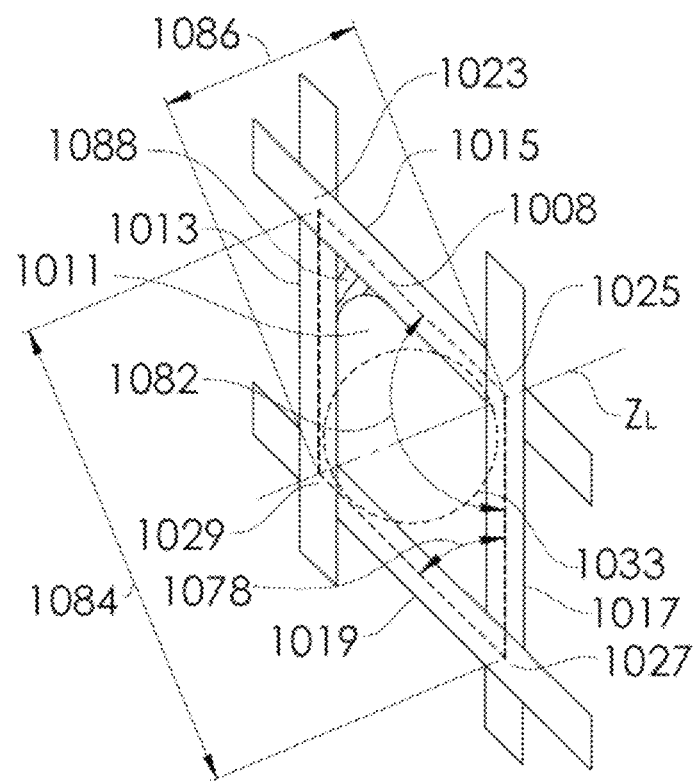
FIG. 19 is a detailed view of FIG. 18 taken within circle 19.

FIG. 18 illustrates a stent 134 (or flow diversion device) having a proximal end 136 and a distal end 138, and a distal opening 140 and a proximal opening 142. The stent 134 is in a curved condition, so that it has a convex side 131 and a concave side 133. The woven or braided mesh may comprise a plurality of diamond-shaped modules 1008 (FIG. 19). The diamond-shaped modules 1008 include diamond-shaped openings 1011, bounded by filaments 1013, 1015, 1017, 1019. The diamond-shaped openings 1011 may each have low flow zones 1088, especially as the angles 1078 are decreased. The flow of blood through the diamond-shaped openings 1011 varies depending upon the total cross-sectional area of the diamond-shaped openings 1011 and the perimeter of the diamond-shaped openings 1011. The diamond-shaped openings 1011 may be considered to act as if they have a theoretical hydraulic diameter 1033. Longitudinal axis ZL is shown in FIG. 19 and extends from a proximal end 136 to a distal end 138 of the stent 134.

In an embodiment of a stent 134 having a fixed diameter, fixed circumference, and a fixed number of filaments, the number of diamond-shaped modules 1008 fitting within the fixed circumference will not change, regardless of how sparsely or densely the braid is formed. Therefore, the module width 1084 (tangent to the diameter) can remain the same dimension, regardless of how sparsely or densely the braid is formed. However, the module length 1086 will be shorter on the concave side 133, and the module length 1086 will be longer on the convex side 131. This can occur when the stent 134 is placed in the curved condition as filament 1015 and filament 1017 slide over one another at crossing 1025 and filament 1013 and filament 1019 slide over one another at crossing 1029, while angle 1082 (and angle across from angle 1082) change. In conjunction, filament 1013 and filament 1015 will swivel in relation to one another at crossing 1023, and filament 1017 and filament 1019 will swivel in relation to one another at crossing 1027 while angle 1078 (and the angle across from angle 1078) changes. For example, along the convex side 131, angle 1078 may be increased and angle 1082 may be reduced. And, along the concave side 133, angle 1078 may be reduced and angle 1082 may be increased. It should be noted that angle 1082 in braiding nomenclature would be two times the "braid angle."

Braid Angle ($\alpha$) = (angle 1082)/2

Thus along the convex side 131, the braid angle ($\alpha$) is reduced and along the concave side 133, the braid angle ($\alpha$) is increased. There is also a mechanical difference between the convex side 131 and the concave side 133, as the convex side 131 may become stiffer than the convex side.

Additionally, average braid angle ($\alpha$) may be changed at one location along the length of the stent 134 (between the proximal end 136 and a distal end 138) in comparison to another location along the length. This may be controlled by varying the braiding process. For example, the average braid angle ($\alpha$) at an intermediate portion 135 of the stent 134 may be made larger than at the braid angle at portions near the proximal end 136 or the distal end 138 of the stent 134. In this manner, a higher filament density portion (having a smaller diamond-shaped opening 1011) may be located at the intermediate portion 135, which may be placed adjacent the neck 82 of the aneurysm 78, thus better inhibiting blood flow into the aneurysm 78. Traditionally, the formula for hydraulic diameter $D_H$ is:

$$D_H = (4 \times A_O)/P_O$$

Where $A_O$ is the area of the diamond-shaped opening, and $P_O$ is the perimeter of the diamond-shaped opening.

In anatomies wherein the artery 80 is curved, and the neck 82 of an aneurysm 78 is located on a convex portion of the curve of the artery 80, the flow through the diamond-shaped opening 1011 may be increased above a desirable level, and may therefore also have an undesirable increased flow into the aneurysm 78.

In some cases, it may be preferred to construct the stent 134 with relatively large braid angles ($\alpha$) (thus a larger angle 1082 and a smaller angle 1078) in order to produce a smaller diamond-shaped opening 1011 (and smaller hydraulic diameter HD) in the stent 134 towards the neck 82 of the aneurysm, and to assure that the stent 134 is not unacceptably stiff. This way, there is greater chance of causing stagnation of the blood at the neck 82 to promote aneurysm embolization and occlusion. Additionally, there will be less possibility of causing damage to the artery 80 or aneurysm 78 because the more flexible stent 134 is also more atraumatic. Additionally, a stiff stent might reside in the artery in a manner that it could actually buckle or project into the aneurysm. This may be particularly problematic in fusiform aneurysms. Although a more flexible stent 134 as described may minimize these problems, it may have reduced column stiffness, and thus may be very difficult to deliver on its own with greater tendency to buckle, kink, stretch, or otherwise deform when being delivered. Thus, the delivery device 6 comprising a self-expandable portion 8 and an elongate support member 10 can improve the safety and reliability of delivering a stent 134 that is more flexible and/or has a smaller braid angle ($\alpha$) because the self-expandable portion 8 may be constructed to be relatively stiffer, which can fully support and/or protect the stent 134 during delivery. The stent 34, 134 characteristics and self-expandable portion 8 characteristics may be matched in order to produce desired mechanical characteristics of the pair during delivery and/or during retrieval, and so that the stent 134 mechanical characteristics and flow (hydraulic diameter of diamond-shaped opening 1011, etc.) characteristics are also desired.

In one embodiment of a system for completely or partially excluding an aneurysm from circulation of blood, the stent 34, 134 and the self-expandable portion 8 have the following characteristics:

|  | Self-Expandable Portion 8 | Stent 34, 134 |
| --- | --- | --- |
| Material | Cobalt-Chromium (CoCr) | Drawn Filled Tube (Nitinol outer shell/platinum inner core) |
| # of Filaments | 18 | 72 |
| Filament diameter | 0.0015 inches | 0.0013 inches |
| Device Diameter | 4.5 mm | 4.5 mm |
| Braid Angle ($\alpha$) (Braid Angle = one-half of angle 1082) | 80° | 65° |
| Collapsed profile | 0.0093 inches | 0.0161 inches |

In another embodiment of a system for completely or partially excluding an aneurysm from circulation of blood, the stent 34, 134 and the self-expandable portion 8 have the following characteristics:

|  | Self-Expandable Portion 8 | Stent 34, 134 |
| --- | --- | --- |
| Material | Cobalt-Chromium (CoCr) | Drawn Filled Tube (Nitinol outer shell/platinum inner core) |
| # of Filaments | 18 | 48 |
| Filament diameter | 0.0015 inches | 0.0015 inches |
| Device Diameter | 4.5 mm | 4.5 mm |
| Braid Angle ($\alpha$) (one-half of angle 1082) | 75° | 75° |
| Collapsed profile | 0.0093 inches | 0.0152 inches |

Figure 20:
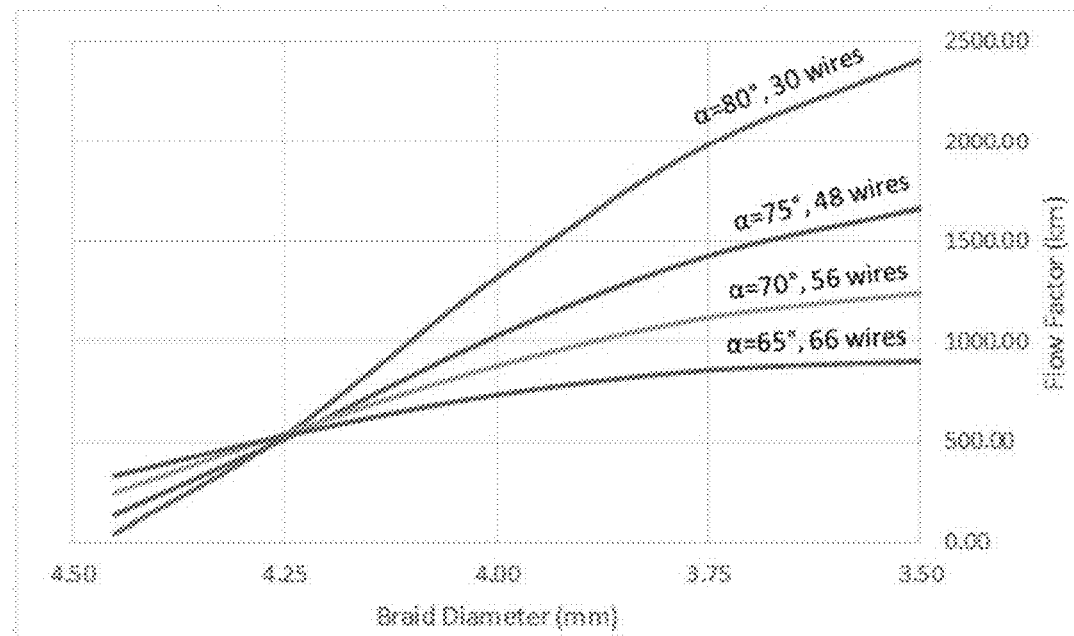
FIG. 20 is a graph of braid diameter vs. radial hoop force.
Figure 21:
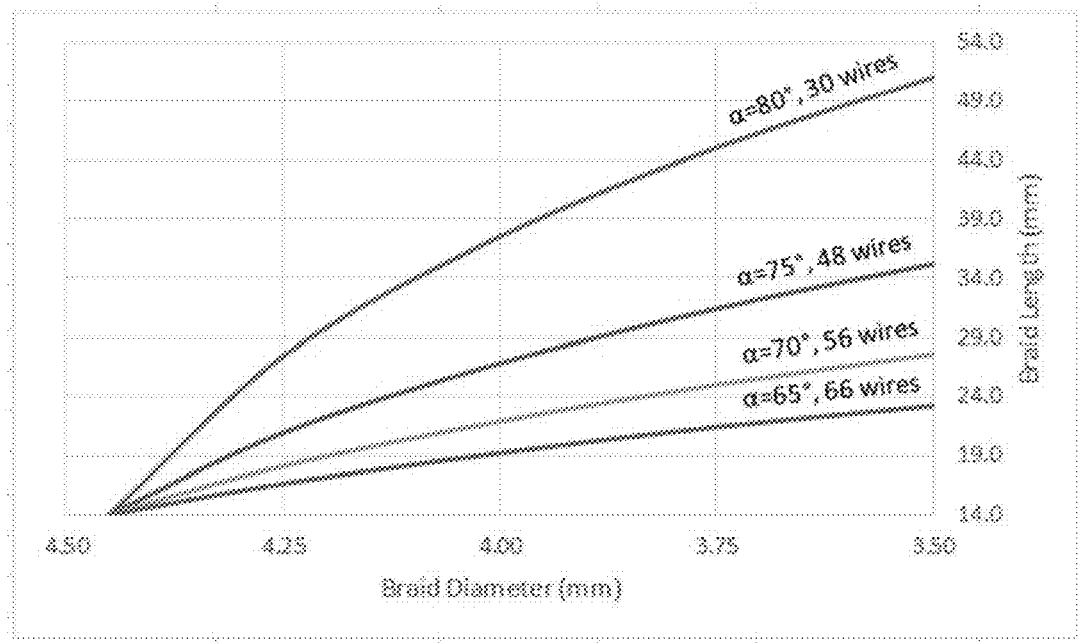
FIG. 21 is a graph of braid diameter vs. bending stiffness.

FIGS. 20 and 21 illustrate the changes in mechanical characteristics of four different braided tubes as their diameters are changed (e.g., by compression, tension, etc.). FIG. 20 illustrates the changes in radial hoop force (N) at different diameters. FIG. 21 illustrates changes in bending stiffness (N/mm) at different diameters. In the graphs of FIGS. 20 and 21, the radial hoop force and the bending stiffness are normalized over a single unit length (total length of the braided tube), thus producing the displayed units of N/mm and N/mm/mm, respectively.

In any of the embodiments, it is possible to include bioresorbable filaments, for example, filaments comprising (PGLA), (PGA), or (PLLA). It is even possible to make a fully bioresorbable mesh device. Bioresorbable metals such as magnesium, magnesium alloys, iron, or iron alloy may also be used to make bioresorbable filaments. In any of the embodiments, it is possible to coat at least some of the permeable shell or filaments with a growth factor, for example a CE34 antibody, in order to encourage the growth of endothelial cells to form a healing cap on an occluded aneurysm. The action of the CE34 antibody is to bind to an endothelial-derived growth factor.

Although the foregoing invention has, for the purposes of clarity and understanding, been described in some detail by way of illustration and example, it will be obvious that certain changes and modifications may be practiced which will still fall within the scope of the appended claims.

What is claimed is:

1. A method for treating an aneurysm in a cerebral vessel, comprising the steps of:
    advancing a system within a lumen of a microcatheter to a position distal to a neck of the aneurysm in the cerebral vessel, wherein the system is coupled to an elongate member having proximal and distal ends, wherein the system comprises:
        an expandable stent having a proximal end, a distal end, and a lumen therebetween, the expandable stent having a constrained state that is configured for delivery through the lumen of the microcatheter, and an expanded state configured for placement within the cerebral vessel adjacent the aneurysm, wherein the expandable stent comprises a tubular mesh structure formed of a plurality of filaments, and
        a delivery device comprising a self-expandable portion having outer and inner surfaces and proximal and distal ends, the proximal end of the self-expandable portion coupled to the elongate member at or near the distal end of the elongate member, the distal end of the self-expandable portion having a distal opening, wherein the self-expandable portion comprises a tubular mesh structure having a constrained state that is configured for delivery through the lumen of the microcatheter, and an expanded state; and
    releasing at least part of the expandable stent and at least part of the self-expandable portion of the delivery device through a distal opening of the microcatheter, wherein the expandable stent is engaged with an outermost surface of the self-expandable portion of the delivery device when the at least part of the expandable stent and the at least part of the self-expandable portion of the delivery device exit through the distal opening, and wherein the distal end of the expandable stent is released in the cerebral vessel distal of the aneurysm neck.

2. The method of claim 1, wherein releasing the at least part of the expandable stent and the at least part of the self-expandable portion through the distal opening of the microcatheter comprises advancing the distal end of the expandable stent and the distal end of the self-expandable portion of the delivery device through the distal opening of the microcatheter.

3. The method of claim 1, wherein both the expandable stent and self-expandable portion are each in the constrained state in the lumen of the microcatheter.

4. The method of claim 1, wherein at least some of the plurality of filaments comprise drawn filled tubes.

5. The method of claim 1, wherein the plurality of filaments comprises a shape memory alloy.

6. The method of claim 1, wherein releasing the at least part of the expandable stent and the at least part of the self-expandable portion through the distal opening of the microcatheter comprises withdrawing the microcatheter proximally while the elongate member is held substantially in place, wherein the expandable stent and self-expandable portion of the delivery device expand to their expanded states.

7. The method of claim 1, wherein the self-expandable portion mechanically engages the expandable stent substantially from the proximal end to the distal end of the expandable stent.

8. The method of claim 1, wherein the self-expandable portion frictionally engages the expandable stent substantially from the proximal end to the distal end of the expandable stent.

9. The method of claim 1, further comprising the step of assessing the placement of the expandable stent relative to the aneurysm neck.

10. The method of claim 9, further comprising the steps of:
    recapturing the at least part of the expandable stent and at least part of the self-expandable portion within the lumen of the microcatheter;
    repositioning the distal end of the microcatheter to a position distal of the neck of the aneurysm; and
    releasing the expandable stent and at least part of the self-expandable portion through the distal opening of the microcatheter, wherein the expandable stent in its expanded state is positioned in the cerebral vessel such that the distal end of the expandable stent is located distal of the aneurysm neck and the proximal end of the expandable stent is located proximal of the aneurysm neck.

11. The method of claim 10, wherein recapturing the at least part of the expandable stent and at least part of the self-expandable portion comprises advancing the microcatheter distally while maintaining traction on the elongate member to recapture the expandable stent and self-expandable portion within the lumen of the microcatheter.

12. The method of claim 1, wherein releasing the at least part of the expandable stent and the at least part of the self-expandable portion through the distal opening of the microcatheter comprises releasing the expandable stent and at least part of the self-expandable portion through the distal opening of the microcatheter, wherein the expandable stent in its expanded state is positioned in the cerebral vessel such that the distal end of the expandable stent is located distal of the aneurysm neck and the proximal end of the expandable stent is located proximal of the aneurysm neck.

13. The method of claim 1, further comprising the steps of:
   advancing the microcatheter distally while applying traction to the proximal end of the elongate member, thereby disengaging the expandable stent and the self-expandable portion, and withdrawing the self-expandable portion of the delivery device into the lumen of the microcatheter.

14. The method of claim 13, further comprising the step of withdrawing the microcatheter and delivery device from the cerebral vessel.

15. The method of claim 1, wherein the expandable stent is completely self-expanding.

16. The method of claim 1, wherein the expandable stent is partially self-expanding.

17. The method of claim 1, wherein the tubular mesh structure of the self-expandable portion comprises a second plurality of filaments.

18. The method of claim 17, wherein the second plurality of filaments comprises a cobalt-chromium alloy.

19. The method of claim 17, wherein the second plurality of filaments each have a diameter of between about 0.0010 inches and 0.0020 inches.

* * * * *